United States Patent
Lipkin et al.

(10) Patent No.: US 10,829,823 B2
(45) Date of Patent: Nov. 10, 2020

(54) COMPOSITIONS AND METHODS FOR THE RAPID DIFFERENTIAL DETECTION OF ZIKA VIRUS

(71) Applicant: THE TRUSTEES OF COLUMBIA UNIVERSITY IN THE CITY OF NEW YORK, New York, NY (US)

(72) Inventors: Walter Ian Lipkin, New York, NY (US); Nischay Mishra, New York, NY (US); Thomas Briese, White Plains, NY (US); Rafal Tokarz, Queens Village, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/085,825

(22) PCT Filed: Mar. 17, 2017

(86) PCT No.: PCT/US2017/023012
§ 371 (c)(1),
(2) Date: Sep. 17, 2018

(87) PCT Pub. No.: WO2017/161302
PCT Pub. Date: Sep. 21, 2017

(65) Prior Publication Data
US 2019/0032152 A1 Jan. 31, 2019

Related U.S. Application Data

(60) Provisional application No. 62/309,770, filed on Mar. 17, 2016, provisional application No. 62/431,550, filed on Dec. 8, 2016.

(51) Int. Cl.
| | | |
|---|---|---|
| *A61K 39/12* | (2006.01) |
| *C12Q 1/70* | (2006.01) |
| *A61K 39/00* | (2006.01) |
| *C12N 7/00* | (2006.01) |
| *C07K 14/005* | (2006.01) |
| *C12Q 1/6888* | (2018.01) |
| *C12Q 1/6806* | (2018.01) |
| *C12Q 1/686* | (2018.01) |

(52) U.S. Cl.
CPC .......... *C12Q 1/6888* (2013.01); *C12Q 1/686* (2013.01); *C12Q 1/6806* (2013.01); *C12Q 1/701* (2013.01); *C12Q 2600/112* (2013.01); *C12Q 2600/16* (2013.01); *C12Q 2600/166* (2013.01)

(58) Field of Classification Search
CPC ...... A61K 2300/00; A61K 39/12; C12N 7/00; C12N 2770/24134; C07K 14/005
See application file for complete search history.

(56) References Cited

U.S. PATENT DOCUMENTS

2013/0217071 A1* 8/2013 Montesclaros ......... C12P 19/34
435/91.2

OTHER PUBLICATIONS

GenBank Accession No. KF383083, 2014: pdf p. 1.*
Shawan et al., "Design and prediction of potential RNAi (siRNA) molecules for 3'UTR PTGS of defferent strains of zika virus", Nature and Science of Sleep, 2015: 37-50.*
Shawan et al., Design and prediction of potential RNAi (siRNA) molecules for 3'UTR PTGS of different strains of zika virus: a computational approach. Nature and Science, Feb. 2015, vol. 13, No. 2, pp. 37-50. Especially abstract; p. 38, col. 2, para 1; p. 48, col. 1, para 2.
KF383083, GenBank Accession No. KF383083. Zika virus strain AnD30332 3'UTR, Mar. 15, 2014 [online]. (Retrieved on Jul. 17, 2017). Retrieved from the internet: <URL: https://www.ncbi.nlm.nih.gov/nuccore/KF383083> Entire document.
Zika Virus, CDC Website—http://www.cdc.gov/zika/. Jun. 2015.
Driggers et al. New England Journal of Medicine Zika virus Infection with Prolonged Maternal Viremia and Fetal Brian Abnormalities., Jun. 2, 2016; 374:2142-2151.
Meaney-Delman et al. Obstetrics and Gynecology Prolonged Detection of Zika Virus RNA in Pregnant Women., Oct. 4, 2016 128(4) 724-730.
Lanciotti et al. Emerg Infect Dis Genetic and serologic properties of Zika virus associated with an epidemic, Yap State, Micronesia, 2007. 2008;14:1232-9. Aug. 8, 2008.

* cited by examiner

Primary Examiner — Barry A Chestnut
(74) Attorney, Agent, or Firm — Leason Ellis LLP

(57) ABSTRACT

This invention relates to compositions and methods for the differential detection of multiple viruses using a one-step assay. The viruses to be detected include Zika, West Nile, dengue (genotype 1-4) and chikungunya viruses. In particular, the invention relates to a method of and assay for differential detection of the viruses using specific primers and probes designed to detect and differentiate between the viruses.

24 Claims, 2 Drawing Sheets

Specification includes a Sequence Listing.

Fig. 1

| ZIKV | DENV | CHIKV | WNV | Rnase P | HSC (with Rnase P) | Interpretation* | Reporting |
|---|---|---|---|---|---|---|---|
| − | − | − | − | + | + | No ZIKV, CHIKV, DENV OR WNV RNA detected by rRT-PCR | negative |
| + | − | − | − | +/− | + | ZIKV RNA detected by rRT-PCR but No CHIKV, DENV OR WNV RNA detected by rRT-PCR | ZIKV positive |
| − | + | − | − | +/− | + | DENV RNA detected by rRT-PCR but No ZIKV, CHIKV OR WNV RNA detected by rRT-PCR | DENV positive |
| − | − | + | − | +/− | + | CHIKV RNA detected by rRT-PCR but No ZIKV, DENV OR WNV RNA detected by rRT-PCR | CHIKV positive |
| − | − | − | + | +/− | + | WNV RNA detected by rRT-PCR but No ZIKV, CHIKV OR DENV RNA detected by rRT-PCR | WNV positive |
| + | + | − | − | +/− | + | ZIKV AND DENV RNA detected by rRT-PCR but No CHIKV OR WNV RNA detected by rRT-PCR | ZIKV, DENV positive |
| + | − | + | − | +/− | + | ZIKV AND CHIKV RNA detected by rRT-PCR but No DENV OR WNV RNA detected by rRT-PCR | ZIKV, CHIKV positive |
| + | − | − | + | +/− | + | ZIKV AND WNV RNA detected by rRT-PCR but No DENV OR CHIKV RNA detected by rRT-PCR | ZIKV, WNV positive |
| − | − | − | − | − | + | Inconclusive rRT-PCR results | Inconclusive |
| − | − | − | − | − | − | Repeat nucleic acid extraction | Invalid |

*Any combination of virus targets may be positive with CII-ArboPlex rRT-PCR assay and more than two agents may also be positive by this test.

| | Contrived DENV 3 samples in urine | | Contrived DENV 3 samples in serum | | Contrived WNV samples in urine | | Contrived WNV samples in serum | | Contrived CHIKV samples in urine | | Contrived CHIKV samples in serum | |
|---|---|---|---|---|---|---|---|---|---|---|---|---|
| | 1X LoD | 2X LoD | 1X LoD | 2X LoD | 1X LoD | 2X LoD | 1X LoD | 2X LoD | 1X LoD | 2X LoD | 1X LoD | 2X LoD |
| 1 | 30.93 | 32.15 | 31.49 | 30.43 | 31.31 | 29.86 | 32.56 | 31.33 | 32.42 | 31.39 | 32.59 | 31.12 |
| 2 | 31.74 | 29.39 | 31.36 | 30.82 | 32.12 | 30.25 | 32.73 | 32.06 | 31.4 | 31.14 | 31.6 | 31.91 |
| 3 | 30.56 | 28.55 | 32.21 | 30.33 | 32.17 | 29.69 | 32.29 | 32.08 | 32.31 | 31.33 | 32.37 | 31.49 |
| 4 | 31.24 | 28.71 | 32.58 | 30.67 | 32.2 | 30.31 | 32.33 | 31.96 | 32.61 | 31.2 | 31.79 | 30.83 |
| 5 | 30.12 | 28.82 | 30.93 | 30.95 | 31.54 | 29.84 | 32.09 | 32.57 | 32.27 | 30.58 | 31.62 | 32.94 |
| 6 | 30.28 | 28.9 | 31.47 | 31.1 | 31.41 | 29.81 | 32.96 | 32.49 | 32.08 | 31.35 | 31.96 | 31.64 |
| 7 | 30.78 | 29.23 | 31.36 | 29.88 | 31.49 | 30.01 | 32.02 | 31.5 | 32.16 | 31.01 | 31.13 | 31.33 |
| 8 | 30.77 | 28.61 | 31.46 | 31.4 | 31.57 | 29.93 | 32.81 | 32.26 | 32.38 | 31.28 | 31.93 | 31.73 |
| 9 | 30.33 | 28.23 | 30.49 | 29.82 | 31.66 | 29.88 | 32.43 | 32.05 | 32.22 | 31.14 | 31.91 | 31.51 |
| 10 | 32.22 | 29.68 | 31.85 | 30.62 | 32.14 | 30.65 | 32.58 | 32.23 | 32.23 | 30.42 | 32.16 | 32.17 |
| 11 | 30.26 | 28.83 | 31.74 | 30.71 | 31.82 | 30.06 | 39.17 | 33.02 | 32.27 | 30.43 | 36.07 | 31.52 |
| 12 | 31.42 | 28.89 | 37.11 | 36.09 | 31.55 | 29.93 | 33.27 | 33.19 | 32.1 | 30.74 | 32.22 | 33.47 |
| 13 | 33.54 | 29.6 | 31.51 | 31.04 | 31.66 | 31.51 | 33.34 | 32.72 | 32.12 | 30.87 | 35.01 | 32.58 |
| Average ct | 31.09 | 29.20 | 31.97 | 31.07 | 31.74 | 30.13 | 33.12 | 32.27 | 32.20 | 30.99 | 32.49 | 31.86 |
| Call rate | 13/13 | 13/13 | 13/13 | 13/13 | 13/13 | 13/13 | 13/13 | 13/13 | 13/13 | 13/13 | 13/13 | 13/13 |
| Call % | 100% | 100% | 100% | 100% | 100% | 100% | 100% | 100% | 100% | 100% | 100% | 100% |

Fig. 2

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
artgttgtca ggcctgctag                                               20

<210> SEQ ID NO 2
<211> LENGTH: 21
<212> TYPE: DNA
<213> ORGANISM: Artificial Sequence
<220> FEATURE:
<223> OTHER INFORMATION: synthetic primer

<400> SEQUENCE: 2
cttgrtttcc cagcktctcc t                                             21

<210> SEQ ID NO 3
<211> LENGTH: 21
<212> TYPE: DNA
<213> ORGANISM: Artificial Sequence
<220> FEATURE:
<223> OTHER INFORMATION: synthetic probe

<400> SEQUENCE: 3
ggggaaagct gtgcagcctg t                                             21

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
catttgctcc gctgtccctg tgaa                                          24

<210> SEQ ID NO 5
<211> LENGTH: 25
<212> TYPE: DNA
<213> ORGANISM: Artificial Sequence
<220> FEATURE:
<223> OTHER INFORMATION: synthetic primer

<400> SEQUENCE: 5
ccactctcct cctgcatgga tggac                                         25

<210> SEQ ID NO 6
<211> LENGTH: 25
<212> TYPE: DNA
<213> ORGANISM: Artificial Sequence
```

```
<220> FEATURE:
<223> OTHER INFORMATION: synthetic probe

<400> SEQUENCE: 6
tgggtcccta ccggaagaac cacgt                                              25

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
actagaggtt agaggagacc ccc                                                23

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
ggcgctctgt gcctggatt                                                     19

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
tggcgttctg tgcctggaat                                                    20

<210> SEQ ID NO 10
<211> LENGTH: 19
<212> TYPE: DNA
<213> ORGANISM: Artificial Sequence
<220> FEATURE:
<223> OTHER INFORMATION: synthetic probe

<400> SEQUENCE: 10
cccagcgtca atatgctgt                                                     19

<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
catctgcacy caagtgtacc a                                                  21

<210> SEQ ID NO 12
<211> LENGTH: 21
<212> TYPE: DNA
<213> ORGANISM: Artificial Sequence
<220> FEATURE:
<223> OTHER INFORMATION: synthetic primer

<400> SEQUENCE: 12
gcgcattttg ccttcgtaat g                                                  21
```

```
<210> SEQ ID NO 13
<211> LENGTH: 18
<212> TYPE: DNA
<213> ORGANISM: Artificial Sequence
<220> FEATURE:
<223> OTHER INFORMATION: synthetic probe

<400> SEQUENCE: 13
aaaagtatct ccaggcgg                                                 18

<210> SEQ ID NO 14
<211> LENGTH: 19
<212> TYPE: DNA
<213> ORGANISM: Artificial Sequence
<220> FEATURE:
<223> OTHER INFORMATION: synthetic primer

<400> SEQUENCE: 14
agatttggac ctgcgagcg                                                19

<210> SEQ ID NO 15
<211> LENGTH: 19
<212> TYPE: DNA
<213> ORGANISM: Artificial Sequence
<220> FEATURE:
<223> OTHER INFORMATION: synthetic primer

<400> SEQUENCE: 15
gagcggctgt ctccacaag                                                19

<210> SEQ ID NO 16
<211> LENGTH: 22
<212> TYPE: DNA
<213> ORGANISM: Artificial Sequence
<220> FEATURE:
<223> OTHER INFORMATION: synthetic probe

<400> SEQUENCE: 16
tctgacctga aggctctgcg cg                                            22
```

COMPOSITIONS AND METHODS FOR THE RAPID DIFFERENTIAL DETECTION OF ZIKA VIRUS

CROSS REFERENCE TO RELATED APPLICATION

The present application is a U.S. National Phase Application under 35 U.S.C. § 371 of International Patent Application No. PCT/US2017/023012, filed Mar. 17, 2017, which claims priority to U.S. Patent Application Ser. No. 62/309,770 filed Mar. 17, 2016 and Ser. No. 62/431,550 filed Dec. 8, 2016, all of which are incorporated by reference as if expressly set forth in their respective entireties here.

STATEMENT OF GOVERNMENT SUPPORT

This invention was made with government support under AI109761 awarded by National Institutes of Health. The government has certain rights in the invention.

FIELD OF THE INVENTION

This invention relates to compositions and methods for the differential detection of multiple viruses using a one-step assay. The viruses to be detected include Zika, West Nile, dengue (genotype 1-4) and chikungunya viruses. In particular, the invention relates to a method of differential detection of the viruses using specific primers and probes designed to detect and differentiate between the viruses.

BACKGROUND OF THE INVENTION

Zika virus (ZIKV) is an emerging mosquito-borne virus that affects several major continents including Africa, Asia, and the Americas, and has been deemed a global emergency by the World Health Organization (WHO). ZIKV infection carries high risk for pregnant women as it has been causally linked to severe fetal brain anomalies such as microcephaly, intracranial calcifications, and fetal brain disruption sequence as well as ocular anomalies (Rasmussen et al. 2016). Furthermore, ZIKV infection likely triggers an increased risk for Guillain-Barré syndrome (Broutet et al. 2016).

In urban and suburban environments, ZIKV is transmitted in a human-mosquito-human transmission cycle. In addition to mosquito transmission, evidence indicates that ZIKV can be transmitted from the mother to the fetus during pregnancy. Additionally, sexual transmission to partners has also been reported. Finally, although the transmission of ZIKV through a blood transfusion has not been reported, it is likely to occur, given the transmission of other, related flaviviruses, through this route.

Zika virus is a flavivirus, closely related to dengue virus (DENV). ZIKV diagnosis is often based on clinical symptoms and epidemiological links Zika virus and dengue virus infections as well as infections from other viruses, i.e., West Nile virus (a flavivirus) and chikungunya virus (an alphavirus), present with similar clinical symptoms causing difficulty in differential diagnosis.

To date there is no method or assay for the differential detection of these four related arboviruses.

SUMMARY OF THE INVENTION

The current invention provides for an assay (i.e., CII-ArboPlex rRT-PCR assay), a multiplex one-step reverse transcription real time polymerase chain reaction test intended for the detection and diagnosis of Zika virus infection by detecting viral RNA in serum and urine specimens (which can be collected simultaneously with the serum specimen from the same patient). The assay can also be used for the differential detection of RNA from dengue virus (DENV types 1-4), Chikungunya virus (CHIKV) and West Nile virus (WNV) in serum and urine samples. ZIKV RNA is typically detectable in serum and/or urine during the acute phase of infection and up to two weeks following onset of symptoms. Positive results with the CII-ArboPlex rRT-PCR assay are indicative of acute viral infection.

The current invention provides compositions, methods, and kits for detecting the presence of nucleic acids of certain arboviruses. Specifically, the current invention allows for the differential detection of certain arboviruses. In particular, the current invention allows for the differential detection of Zika virus as well as dengue, chikungunya, and West Nile virus in a one-step assay using a polymerase chain reaction format. The method and assay of the invention is rapid, inexpensive, sensitive, and specific, and allows for the detection and diagnosis of Zika virus, as well as dengue, chikungunya, and West Nile virus. In certain embodiments, the current invention allows the detection and the determination of which specific virus or viruses are found in a single sample. In one aspect, the invention is primers and probes that can not only detect the viruses in a single sample, but differentiate which virus or viruses are contained in a single sample.

In certain aspects, the invention provides a method for detecting a nucleic acid of Zika, dengue, chikungunya, and West Nile virus in a one-step assay, i.e., a single sample. In some embodiments, the methods comprise amplifying the nucleic acid of the viruses in the presence of a detectably-labeled oligonucleotide probe. In some embodiments, the methods comprise amplifying the nucleic acid of the viruses using a primer, wherein the primer comprises SEQ ID NOs: 1, 2, 4, 5, 7, 8, 9, 11, or 12. In some embodiments, the methods comprise amplifying the nucleic acid of the viruses using more than one primer, in primer pair or groups, wherein the primer pairs or groups comprise: SEQ ID NO: 1 and SEQ ID NO: 2; SEQ ID NO: 4 and SEQ ID NO: 5; SEQ ID NO: 7, SEQ ID NO: 8, and SEQ ID NO. 9; and SEQ ID NO: 11 and SEQ ID NO: 12. In some embodiments, the oligonucleotide probe comprises SEQ ID NOs: 3, 6, 10, or 13. In some embodiments, the methods comprise amplifying the nucleic acid of the viruses using more than one primer, in primer pair or groups, and detecting the presence of the nucleic acids with a detectably-labeled probe, wherein the primer pairs or groups and probes comprise: SEQ ID NO: 1, SEQ ID NO: 2, and SEQ ID NO: 3; SEQ ID NO: 4, SEQ ID NO: 5, and SEQ ID NO: 6; SEQ ID NO: 7, SEQ ID NO: 8, SEQ ID NO. 9, and SEQ ID NO: 10; and SEQ ID NO: 11, SEQ ID NO: 12, and SEQ ID NO: 13. In some embodiments of the method, all of the primer groups and probes are used to detect the nucleic acid of the viruses in one sample at the same time, i.e., simultaneously. In some embodiments of the method, all of the primer groups and probes are used to detect the nucleic acid of the viruses in one sample at consecutive times, i.e., concurrently. In some embodiments, the nucleic acid to be detected is RNA. In some embodiments, the nucleic acid to be detected is cDNA.

In certain embodiments, the probe comprises a detectable moiety. The detectable moiety can be any detectable moiety known to one of skill in the art without limitation. For example, the detectable moiety can be a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes.

In certain embodiments, the probe comprises a quencher moiety. The quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes, Iowa Black™, or Dabcyl.

In certain embodiments, the methods comprise amplifying the nucleic acid of the Zika, dengue, chikungunya, and West Nile viruses in the presence of a detectably-labeled nucleic acid probe which comprises a fluorescent moiety and a quencher moiety. In certain embodiments, fragmentation of the detectably-labeled probe by a template-dependent nucleic acid polymerase with 5'-3' nuclease activity separates the fluorescent moiety from the quencher moiety. In certain embodiments, the fragmentation of the probe and thus the presence of the nucleic acid of the virus can be detected by monitoring emission of fluorescence.

The present invention also provides methods of detecting Zika, dengue, chikungunya, and West Nile viruses in a one-step assay, i.e., a single sample. In some embodiments, the methods comprise amplifying a nucleic acid of Zika, dengue, chikungunya, and West Nile viruses with at least one oligonucleotide comprising a sequence selected from the group consisting of SEQ ID NO: 1, SEQ ID NO: 2, SEQ ID NO: 4, SEQ ID NO: 5, SEQ ID NO: 7, SEQ ID NO: 8, SEQ ID NO: 9, SEQ ID NO:11, and SEQ ID NO: 12 under conditions to allow for initiation of amplification of at least part of the nucleotide sequence from the oligonucleotide; and detecting the amplified nucleic acid, thereby detecting the viruses. In some embodiments, the methods comprise amplifying the nucleic acid of the viruses using more than one primer, in primer pair or groups, wherein the primer pairs or groups comprise: SEQ ID NO: 1 and SEQ ID NO: 2; SEQ ID NO: 4 and SEQ ID NO: 5; SEQ ID NO: 7, SEQ ID NO: 8, and SEQ ID NO. 9; and SEQ ID NO: 11 and SEQ ID NO: 12. In some embodiments, the oligonucleotide probe comprises SEQ ID NOs: 3, 6, 10, or 13. In some embodiments, the methods comprise amplifying the nucleic acid of the viruses using more than one primer, in primer pair or groups, and detecting the presence of the nucleic acids with a detectably-labeled probe, wherein the primer pairs or groups and probes comprise: SEQ ID NO: 1, SEQ ID NO: 2, and SEQ ID NO: 3; SEQ ID NO: 4, SEQ ID NO: 5, and SEQ ID NO: 6; SEQ ID NO: 7, SEQ ID NO: 8, SEQ ID NO. 9, and SEQ ID NO: 10; and SEQ ID NO: 11, SEQ ID NO: 12, and SEQ ID NO: 13. In some embodiments of the method, all of the primer groups and probes are used to detect the nucleic acid of the viruses in one sample at the same time, i.e., simultaneously. In some embodiments of the method, all of the primer groups and probes are used to detect the nucleic acid of the viruses in one sample at consecutive times, i.e., concurrently. In some embodiments, the nucleic acid is RNA. In some embodiments, the nucleic acid is cDNA.

In certain embodiments, the probe comprises a detectable moiety. The detectable moiety can be any detectable moiety known to one of skill in the art without limitation. For example, the detectable moiety can be a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes.

In certain embodiments, the probe comprises a quencher moiety. The quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes, Iowa Black™, or Dabcyl.

In certain embodiments, the methods comprise amplifying the nucleic acid of the Zika, dengue, chikungunya, and West Nile viruses in the presence of a detectably-labeled nucleic acid probe which comprises a fluorescent moiety and a quencher moiety. In certain embodiments, fragmentation of the detectably-labeled probe by a template-dependent nucleic acid polymerase with 5'-3' nuclease activity separates the fluorescent moiety from the quencher moiety. In certain embodiments, the fragmentation of the probe and thus the presence of the nucleic acid of the virus can be detected by monitoring emission of fluorescence.

In addition to the foregoing methods, the present invention further provides nucleic acid primers and probes for detecting a nucleic acid of the Zika, dengue, chikungunya, and West Nile viruses. In certain aspects, the invention provides a nucleic acid primer for detecting the Zika, dengue, chikungunya, and West Nile viruses.

In certain embodiments, the invention provides for a nucleic acid primer for detecting Zika virus comprising SEQ ID NO: 1 and/or SEQ ID NO: 2. In certain embodiments, the invention provides for a nucleic acid primer for detecting West Nile virus comprising SEQ ID NO: 4 and/or SEQ ID NO: 5. In certain embodiments, the invention provides for a nucleic acid primer for detecting a dengue virus comprising SEQ ID NO: 7, SEQ ID NO: 8 and/or SEQ ID NO: 9. In certain embodiments, the invention provides for a nucleic acid primer for detecting chikungunya virus comprising SEQ ID NO: 11 and/or SEQ ID NO: 12.

In other aspects, the invention provides a nucleic acid probe for detecting the Zika, dengue, chikungunya, and West Nile viruses. In certain embodiments, the invention provides for a nucleic acid probe for detecting Zika virus comprising SEQ ID NO: 3. In certain embodiments, the invention provides for a nucleic acid probe for detecting West Nile virus comprising SEQ ID NO: 6. In certain embodiments, the invention provides for a nucleic acid probe for detecting a dengue virus comprising SEQ ID NO: 10. In certain embodiments, the invention provides for a nucleic acid probe for detecting chikungunya virus comprising SEQ ID NO: 13.

In certain embodiments, the invention provides a nucleic acid probe comprising a fluorescent moiety and a quencher moiety. In certain embodiments, the fluorescent moiety is positioned relative to the quencher moiety such that a photon emitted by the fluorescent moiety is absorbed by the quencher moiety when the probe is intact. Fragmentation of the probe by an enzyme with 5' nuclease activity separates the fluorescent moiety from the quencher moiety such that a photon emitted by the fluorescent moiety can be detected.

In other aspects, the invention provides a kit for the detection of a nucleic acid of the Zika, dengue, chikungunya, and West Nile viruses and/or the detection of the Zika, dengue, chikungunya, and West Nile virus. In certain embodiments, the kit comprises a combination of one or more of the primers and probes of the invention. In certain embodiments the kit comprises one or more primers chosen from the group consisting of SEQ ID NOs: 1, 2, 4, 5, 7, 8, 9, 11, and 12. In certain embodiments, the kit comprises one or more probes chosen from the group consisting of SEQ ID NOs: 3, 6, 10, and 13. In certain embodiments, the kit further comprises primers and probes for positive control sequences. In certain embodiments, the kit further comprises primers and probes for detecting human RNase. In certain embodiments, the kit comprises primers and probe comprising SEQ ID NOs: 14-16.

In certain embodiments, the kits of the invention comprise an oligonucleotide useful as a nucleic acid probe, wherein one or more detectable moieties is attached to the nucleic acid probe. In certain embodiments, the one or more detectable moieties is a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes.

In certain embodiments, the kits of the invention comprise an oligonucleotide useful as a nucleic acid probe, wherein at least one quencher moiety is attached to the nucleic acid probe. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes, Iowa Black™, or Dabcyl. In other embodiments, the probe comprises at least one detectable moiety, e.g. a fluorescent moiety and at least one quencher moiety. In one embodiment, the probes are labeled using the dual labeled BHQ®.

In certain embodiments, the kits of invention comprise a thermostable DNA polymerase. In certain embodiments, the thermostable DNA polymerase has reverse transcription activity. In certain embodiments, the kits of the invention additionally comprise instructions for detecting a nucleic acid of Zika, dengue, chikungunya, and West Nile and/or the Zika, dengue, chikungunya, and West Nile virus, according to the methods of the invention. In certain embodiments, the kit of the invention includes controls including but not limited to positive controls for all of the viruses and human nucleic acid, and negative controls.

BRIEF DESCRIPTION OF THE FIGURES

FIG. 1 is a table setting forth the interpretation of the assay results and reporting instructions.

FIG. 2 is a table of results of the validation of CII-ArboPlex rRT-PCR Assay with contrived serum and urine samples spiked with dengue, chikungunya and West Nile viruses.

DETAILED DESCRIPTION OF THE INVENTION

In accordance with the present invention, there may be numerous tools and techniques within the skill of the art, such as those commonly used in molecular immunology, cellular immunology, pharmacology, and microbiology. See, e.g., Sambrook et al. (2001) *Molecular Cloning: A Laboratory Manual,* 3rd ed. Cold Spring Harbor Laboratory Press: Cold Spring Harbor, N.Y.; Ausubel et al. eds. (2005) *Current Protocols in Molecular Biology*, John Wiley and Sons, Inc.: Hoboken, N.J.; Bonifacino et al. eds. (2005) *Current Protocols in Cell Biology*, John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons, Inc.: Hoboken, N.J.

An "amplification reaction" refers to any reaction (e.g., chemical, enzymatic, or other type of reaction) which results in increased copies of a template nucleic acid sequence or increased signal indicating the presence of the template. Amplification reactions include, but are not limited to, the polymerase chain reaction (PCR) and ligase chain reaction (LCR) (see U.S. Pat. Nos. 4,683,195 and 4,683,202; PCR Protocols: A Guide to Methods and Applications (Innis et al., eds, 1990)), strand displacement amplification (SDA) (Walker, et al., *Nucleic Acids Res.* 20(7):1691-6 (1992); Walker PCR Methods Appl 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch, et al., *Genet. Anal.* 15(2):35-40 (1999)) branched DNA signal amplification (bDNA) (Iqbal, et al., *Mol. Cell. Probes* 13(4):315-320 (1999)) and Q-Beta Replicase (Lizardi, et al., *Bio/Technology* 6:1197 (1988)).

As used herein, a "sample" refers to any substance containing or presumed to contain nucleic acid. The sample can be of natural or synthetic origin and can be obtained by any means known to those of skill in the art. The sample can be a sample of tissue or fluid isolated from an individual or individuals, including, but not limited to, for example, skin, plasma, serum, whole blood, spinal fluid, semen, seminal fluid, lymph fluid, synovial fluid, urine, tears, blood cells, organs, tumors, bronchio-alveolar lavage, and also to samples of in vitro cell culture constituents (including but not limited to conditioned medium resulting from the growth of cells in cell culture medium, recombinant cells and cell components). A nucleic acid can be obtained from a biological sample by any procedure known in the art. Preferred samples including serum and urine.

As used herein, the term "subject" means any organism including, without limitation, a mammal such as a mouse, a rat, a dog, a guinea pig, a ferret, a rabbit and a primate. In the preferred embodiment, the subject is a human being, a pet or livestock animal.

The term "patient" as used in this application means a human subject.

The terms "detection", "detect", "detecting" and the like as used herein means to discover the presence or existence of.

The terms "differentiate", "differential", and the like as used herein means to identify or recognize as different.

The term "arbovirus" as used herein means viruses that are transmitted by mosquitoes, ticks, or other arthropods, which includes Zika, dengue, West Nile and chikungunya, virus as well as yellow fever and encephalitis.

As used herein, the terms "nucleic acid," "polynucleotide" and "oligonucleotide" refer to primers, probes, oligomer fragments to be detected, oligomer controls and unlabeled blocking oligomers and is generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, $N_6$-methyl-adenine, $N_6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N_6$-isopentenyladenine, 1-methylguanine, 1-methylinosine, 2,2-dimethylguanine, 2-methyladenine, 2-methylguanine, 3-methylcytosine, 5-methylcytosine, $N_6$-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-$N_6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611, 5,955,589, 5,844,106, 5,789,562, 5,750,343, 5,728,525, and 5,679,785.

Furthermore, a nucleic acid, polynucleotide or oligonucleotide can comprise one or more modified sugar moieties including, but not limited to, arabinose, 2-fluoroarabinose, xylulose, and a hexose.

It is not intended that the present invention be limited by the source of a nucleic acid, polynucleotide or oligonucleotide. A nucleic acid, polynucleotide or oligonucleotide can be from a human or non-human mammal, or any other organism, or derived from any recombinant source, synthesized in vitro or by chemical synthesis. A nucleic acid, nucleotide, polynucleotide or oligonucleotide may be DNA, RNA, cDNA, DNA-RNA, locked nucleic acid (LNA), peptide nucleic acid (PNA), a hybrid or any mixture of the same, and may exist in a double-stranded, single-stranded or partially double-stranded form. A nucleic acid may also be a derivative nucleic acid as described in U.S. Pat. No. 5,696,248. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

There is no intended distinction in length between the terms nucleic acid, polynucleotide and oligonucleotide, and these terms will be used interchangeably. These terms include double- and single-stranded DNA, as well as double- and single-stranded RNA. Oligonucleotides of the invention may be used as primers and/or probes. Thus oligonucleotides referred to herein as "primers" may act as probes and oligonucleotides referred to as "probes" may act as primer in some embodiments.

The term "residue" as used herein refers to a nucleotide or base within a nucleic acid as defined above. A residue can be any nucleotide known to one of skill in the art without limitation, including all of the biologically occurring nucleotides and non-biologically occurring nucleotides described above.

The term "primer" refers to an oligonucleotide which is capable of acting as a point of initiation of polynucleotide synthesis along a template nucleic acid strand when placed under conditions that permit synthesis of a primer extension product that is complementary to the template strand. The primer can be obtained from a recombinant source, as in a purified restriction fragment, or produced synthetically. Primer extension conditions typically include the presence of four different deoxyribonucleoside triphosphates and an agent with polymerization activity such as DNA polymerase or reverse transcriptase, in a suitable buffer (a "buffer" can include substituents which are cofactors, or which affect pH, ionic strength), and at a suitable temperature. The primer is preferably single-stranded for maximum efficiency in amplification. Primers of the invention may be between 5 to 500 nucleotides, and in some embodiments will have at least 10, 20, 30, 25, 30, 40, 50, 75, or 100 nucleotides and/or have fewer than 500, 300, 200, 100, 90, 80, 70, 60, 50, 40, 30, 25, or 20 nucleotides.

The term "hybridize" refers to binding of a single-stranded nucleic acid or a locally single-stranded region of a double-stranded nucleic acid to another single-stranded nucleic acid or a locally single-stranded region of a double-stranded nucleic acid having a complementary sequence. As one of skill in the art is aware, it is not necessary for two nucleic acid strands to be entirely complementary to hybridize to each other. Depending on the hybridization conditions, a nucleic acid can hybridize to its complement even if there are few, some, or many mismatches, deletions, or additions in one or both strands. In certain embodiments, the primers and probes of the invention can hybridize to an at least partially complementary nucleic acid selectively, as defined below. In certain embodiments, the primers and probes of the invention can hybridize to an at least partially complementary sequence under stringent conditions.

As used herein, the term "probe" refers to an oligonucleotide which can form a duplex structure with a region of a nucleic acid, due to complementarity of at least one sequence in the probe with a sequence in the region. The probe, preferably, does not contain a sequence complementary to sequence(s) of a primer. As discussed below, the probe can be labeled or unlabeled. The 3' terminus of the probe can be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3' hydroxyl or by using a nucleotide that lacks a 3' hydroxyl such as a dideoxynucleotide.

The term "detectable moiety" as used herein refers to any atom or molecule which can be used to provide a detectable (optionally quantifiable) signal, and which can be attached to a nucleic acid or protein. Detectable moieties may provide signals detectable by fluorescence, radioactivity, colorimetry, gravimetry, X-ray diffraction or absorption, magnetism, enzymatic activity, and the like. Convenient detectable moieties for the present invention include those that facilitate detection of the size of an oligonucleotide fragment.

The term "fluorescent moiety" as used herein refers to a chemical moiety that can emit light under conditions appropriate for the particular moiety. Typically, a particular fluorescent moiety can emit light of a particular wavelength following absorbance of light of shorter wavelength. The wavelength of the light emitted by a particular fluorescent moiety is characteristic of that moiety. Thus, a particular fluorescent moiety can be detected by detecting light of an appropriate wavelength following excitation of the fluorescent moiety with light of shorter wavelength. Examples of fluorescent moieties that can be used in the methods and compositions of the present invention include, but are not limited to, fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes.

The term "quencher moiety" as used herein refers to a chemical moiety that can absorb energy emitted by a fluorescent moiety when the quencher moiety is sufficiently close to the fluorescent moiety, for example, when both the quencher and fluorescent moiety are linked to a common polynucleotide. This phenomenon is generally known in the art as fluorescent resonance energy transfer ("FRET"). A quencher moiety can re-emit the energy absorbed from a fluorescent moiety in a signal characteristic for that quencher moiety, and thus a quencher can also be a "fluorescent moiety." Alternatively, a quencher moiety may dissipate the energy absorbed from a fluorescent moiety as heat.

As defined herein, "5' to 3' nuclease activity" or "5' nuclease activity" refers to that activity of an enzyme whereby nucleotides are removed from the 5' end of an oligonucleotide in a sequential manner. The 5' nuclease activity can be a 5' to 3' exonuclease activity or a 5' to 3' endonuclease activity. For example, many template-specific nucleic acid polymerases exhibit a 5' to 3' exonuclease activity that is traditionally associated with some DNA polymerases, (i.e., *E. coli* DNA polymerase I has this activity whereas the Klenow fragment of *E. coli* DNA polymerase I does not). The 5' to 3' exonuclease activity can also cleave a substrate nucleic acid more than one phosphodiester bond (nucleotide) from the 5' end of the substrate.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Unless otherwise explained, all technical and scientific terms used herein have the same meaning as commonly understood by one of ordinary skill in the art to which this disclosure belongs.

Primer and Probes for Detection of Arboviruses

The current invention provides for isolated nucleic acid sequences such as primers and probes from specific portions of the viral genomes, including the 3'UTR of the Zika and dengue virus, the NS5 portion of the West Nile viral genome, and the NSP2 portion of the chikungunya viral genome. These specific primers and probes were designed considering the possible cross-reactivity based upon sequence alignments and assay sensitivity, thus, the primers and probes of the current invention are particularly useful in that they can be used in one single sample and/or reaction to detect and differentiate four different arboviruses, including Zika, dengue, West Nile, and chikungunya.

Additionally, the primers and probes of the current invention are non-naturally occurring compositions. The arboviruses from which the oligonucleotides derive are flaviruses (ZKV, DKV, and WNV) and alphavirus (CHV) all of which are single stranded RNA viruses. As such, the primers and probes of the current invention comprise cDNA that do not occur in nature and the nucleic acid sequences of the current invention are markedly different in structure from naturally occurring viral RNA sequences.

In one aspect, the invention provides for at least one primer that is useful in detecting the presence of a nucleic acid of Zika virus and/or the Zika virus itself. In certain embodiments, the primer comprises the nucleotide sequence of SEQ ID NO: 1 or SEQ ID NO: 2. In certain embodiments, the invention is directed to a primer set comprising the primers comprising the nucleotide sequence of SEQ ID NO: 1 and SEQ ID NO: 2.

In one aspect, the invention provides for at least one primer that is useful in detecting the presence of a nucleic acid of West Nile virus and/or the West Nile virus itself. In certain embodiments, the primer comprises the nucleotide sequence of SEQ ID NO: 4 or SEQ ID NO: 5. In certain embodiments, the invention is directed to a primer set comprising the primers comprising the nucleotide sequence of SEQ ID NO: 4 and SEQ ID NO: 5.

In one aspect, the invention provides for at least one primer that is useful in detecting the presence of a nucleic acid of dengue virus and/or the dengue virus itself. In certain embodiments, the primer comprises the nucleotide sequence of SEQ ID NO: 7, SEQ ID NO: 8 or SEQ ID NO: 9. In certain embodiments, the invention is directed to a primer set comprising the primers comprising the nucleotide sequence of SEQ ID NO: 7, SEQ ID NO: 8, and SEQ ID NO: 9.

In one aspect, the invention provides for at least one primer that is useful in detecting the presence of a nucleic acid of chikungunya virus and/or the chikungunya virus itself. In certain embodiments, the primer comprises the nucleotide sequence of SEQ ID NO: 11 or SEQ ID NO: 12. In certain embodiments, the invention is directed to a primer set comprising the primers comprising the nucleotide sequence of SEQ ID NO: 11 and SEQ ID NO: 12.

One of skill in the art would understand that some bases can be deleted from or added to the end of SEQ ID NOs: 1, 2, 4, 5, 7, 8, 9, 11, and 12, and said primers can still amplify the nucleic acid. Accordingly, this invention includes primers wherein some bases are deleted or added to sequences of SEQ ID NOs: 1, 2, 4, 5, 7, 8, 9, 11, and 12.

In certain aspects, the invention is directed to oligonucleotide probes comprising isolated nucleic acids as described herein, which probes are suitable for hybridization under suitable conditions to nucleic acids from Zika virus. In certain embodiments, the probe comprises the nucleic acid of SEQ ID NO: 3.

In certain aspects, the invention is directed to oligonucleotide probes comprising isolated nucleic acids as described herein, which probes are suitable for hybridization under suitable conditions to nucleic acids from West Nile virus. In certain embodiments, the probe comprises the nucleic acid of SEQ ID NO: 7.

In certain aspects, the invention is directed to oligonucleotide probes comprising isolated nucleic acids as described herein, which probes are suitable for hybridization under suitable conditions to nucleic acids from dengue virus. In certain embodiments, the probe comprises the nucleic acid of SEQ ID NO: 11.

In certain aspects, the invention is directed to oligonucleotide probes comprising isolated nucleic acids as described herein, which probes are suitable for hybridization under suitable conditions to nucleic acids from chikungunya virus. In certain embodiments, the probe comprises the nucleic acid of SEQ ID NO: 13.

The nucleic acid primers and probes of the invention can be prepared by any method known to one of skill in the art without limitation.

In addition to the probe nucleotide sequence, the probe can comprise additional nucleotide sequences or other moieties that do not inhibit the methods of the instant invention. In convenient embodiments of the invention, the probe can comprise additional nucleotide sequences or other moieties that facilitate the methods of the instant invention. For instance, the probe can be blocked at its 3' terminus to prevent undesired nucleic acid polymerization priming by the probe. Also, moieties may be present within the probe that stabilize or destabilize hybridization of the probe or probe fragments with the nucleotide sequence. The probes of the invention can also comprise modified, non-standard, or derivatized nucleotides as defined above.

In certain embodiments of the invention, the probe can comprise a detectable moiety. The detectable moiety can be any detectable moiety known by one of skill in the art without limitation. Further, the detectable moiety can be detectable by any means known to one of skill in the art without limitation. For example, the detectable moiety can be detectable by spectroscopic, photochemical, biochemical, immunochemical, or chemical means.

A variety of detectable moieties that can be used to detect the probes of the invention, as well as methods for their linkage to the probe, are known to the art and include, but are not limited to, enzymes (e.g., alkaline phosphatase and horseradish peroxidase) and enzyme substrates, radioactive moieties, fluorescent moieties, chromophores, chemiluminescent labels, electrochemiluminescent labels, such as Origin™ (Igen, Rockville, Md.), ligands having specific binding partners, or any other labels that may interact with each other to enhance, alter, or diminish a signal. Should a 5' nuclease reaction be performed using a thermostable DNA polymerase at elevated temperatures, the detectable moiety should not be degraded or otherwise rendered undetectable by such elevated temperatures.

In certain embodiments, the detectable moiety can be a fluorescent moiety. The fluorescent moiety can be any fluorescent moiety known to one of skill in the art without limitation. In general, fluorescent moieties with wide Stokes shifts are preferred, allowing the use of fluorometers with filters rather than monochromometers and increasing the efficiency of detection. In certain embodiments, the fluorescent moiety can be selected from the group consisting of fluorescein-family dyes (Integrated DNA Technologies, Inc., Coralville, Iowa), polyhalofluorescein-family dyes, hexachlorofluorescein-family dyes, coumarin-family dyes (Molecular Probes, Inc., Eugene, Or), rhodamine-family dyes (Integrated DNA Technologies, Inc.), cyanine-family dyes, oxazine-family dyes, thiazine-family dyes, squaraine-family dyes, chelated lanthanide-family dyes, BODIPY®-family dyes (Molecular Probes, Inc.), and 6-carboxyfluorescein (FAM™) (Integrated DNA Technologies, Inc.). Other examples of fluorescent moieties that can be used in the probes, methods, and kits of the invention can be found in U.S. Pat. Nos. 6,406,297, 6,221,604, 5,994,063, 5,808,044, 5,880,287, 5,556,959, and 5,135,717.

In other embodiments, the detectable moiety can be a detectable moiety other than a fluorescent moiety. Among radioactive moieties, $^{32}$P-labeled compounds are preferred. Any method known to one of skill in the art without limitation may be used to introduce $^{32}$P into a probe. For example, a probe may be labeled with $^{32}$P by 5' labeling with a kinase or by random insertion by nick translation. Detectable moieties that are enzymes can typically be detected by their activity. For example, alkaline phosphatase can be detected by measuring fluorescence produced by action of the enzyme on appropriate substrate compounds. Where a member of specific binding partners are used as detectable moieties, the presence of the probe can be detected by detecting the specific binding of a molecule to the member of the specific binding partner. For example, an antigen can be linked to the probe, and a monoclonal antibody specific for that antigen can be used to detect the presence of the antigen and therefore the probe. Other specific binding partners that can be used as detectable moieties include biotin and avidin or streptavidin, IgG and protein A, and numerous other receptor-ligand couples well-known to the art. Still other examples of detectable moieties that are not fluorescent moieties can be found in U.S. Pat. Nos. 5,525,465, 5,464,746, 5,424,414, and 4,948,882.

The above description of detectable moieties is not meant to categorize the various labels into distinct classes, as the same label may serve in several different modes. For example, $^{125}$I may serve as a radioactive moiety or as an electron-dense reagent. Horseradish peroxidase may serve as enzyme or as antigen for a monoclonal antibody. Further, one may combine various detectable moieties for desired effect. For example, one might label a probe with biotin, and detect its presence with avidin labeled with $^{125}$I, or with an anti-biotin monoclonal antibody labeled with horseradish peroxidase. Other permutations and possibilities will be readily apparent to those of ordinary skill in the art, and are considered as equivalents within the scope of the instant invention.

The method of linking or conjugating the detectable moiety to the probe depends, of course, on the type of detectable moiety or moieties used and the position of the detectable moiety on the probe.

The detectable moiety may be attached to the probe directly or indirectly by a variety of techniques. Depending on the precise type of detectable moiety used, the detectable moiety can be located at the 5' or 3' end of the probe, located internally in the probe's nucleotide sequence, or attached to spacer arms of various sizes and compositions to facilitate signal interactions. Using commercially available phosphoramidite reagents, one can produce oligonucleotides containing functional groups (e.g., thiols or primary amines) at either terminus via an appropriately protected phosphoramidite, and can attach a detectable moiety thereto using protocols described in, for example, PCR Protocols: A Guide to Methods and Applications, ed. by Innis et al., Academic Press, Inc., 1990.

In certain embodiments, the detectable moiety can be attached to the 5' end of the probe. In certain embodiments, the detectable moiety can be attached to the 3' end of the probe. In other embodiments, the detectable moiety can be attached to the probe at a residue that is within the probe. The detectable moiety can be attached to any portion of a residue of the probe. For example, the detectable moiety can be attached to a sugar, phosphate, or base moiety of a nucleotide in the probe. In other embodiments, the detectable moiety can be attached between two residues of the probe.

In certain embodiments of the invention, the probe can comprise a fluorescent moiety and a quencher moiety. In such embodiments, the fluorescent moiety can be any fluorescent moiety known to one of skill in the art, as described above. Further, the quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes (including the quenchers described in WO 01/86001), Iowa Black™. or Dabcyl (Integrated DNA Technologies, Inc.). Other examples of specific quencher moieties include, for example, but not by way of limitation, TAMRA (N,N,N', N'-tetramethyl-6-carboxyrhodamine) (Molecular Probes, Inc.), DABCYL (4-(4'-dimethylaminophenylazo)benzoic acid), Iowa Black™. (Integrated DNA Technologies, Inc.), Cy3™ (Integrated DNA Technologies, Inc.) or Cy5™ (Integrated DNA Technologies, Inc.). Other examples of quencher moieties that can be used in the probes, methods, and kits of the invention can be found in U.S. Pat. Nos. 6,399,392, 6,348,596, 6,080,068, and 5,707,813.

In certain embodiments, the quencher moiety can be attached to the 5' end of the probe. In certain embodiments, the quencher moiety can be attached to the 3' end of the probe. In other embodiments, the quencher moiety can be attached to the probe at a residue that is within the probe. The quencher moiety can be attached to any portion of a residue of the probe. For example, the quencher moiety can be attached to a sugar, phosphate, or base moiety of a nucleotide in the probe. In other embodiments, the quencher moiety can be attached between two residues of the probe.

Exemplary combinations of fluorescent moieties and quencher moieties that can be used in this aspect of the invention include, but are not limited dual-labeled BHQ® Probes. Dual-labeled BHQ probes are linear, dual labeled 5'-3' exonuclease probes incorporating a fluorophore and quencher covalently attached to the 5' and 3' ends of the oligonucleotide, respectively. Fluorescence signal is generated through the 5' exonuclease activity of Taq polymerase, which cleaves off the fluorescent dye-labeled nucleotide from the probe during digestion of the probe hybridized to its complementary sequence in the target strand and thus separating quencher from fluorophore.

In particular, the exemplified probe for the detection of Zika virus, SEQ ID NO: 3, is modified at the 5' end with CAL Fluor Red 610 and the 3' end with BHQ-2.

The exemplified probe for the detection of West Nile Virus, SEQ ID NO: 7, is modified at the 5' end with Quasar 670 and the 3' end with BHQ-2.

The exemplified probe for the detection of dengue virus, SEQ ID NO: 11, is modified at the 5' end with CAL Fluour Orange 56 and the 3' end with BHQ-1 plus.

The exemplified probe for detection of chikuyunga virus, SEQ ID NO: 13, is modified at the 5' end with FAM and the 3' end with BHQ-1 plus.

Methods of Multiplex Detection of Arboviruses

The present invention provides methods for using nucleic acid primers and probes to detect a nucleic acid of certain arboviruses and/or the virus itself. In some aspects, the present invention provides methods for using nucleic acid primers and probes to quantify a nucleic acid of certain arboviruses in a sample. Any method for using nucleic acid primers and probes to detect a nucleic acid known to one of skill in the art or later developed without limitation can be used to detect a nucleic acid of a detectable arbovirus, as described herein. In certain embodiments, the methods provide using a primer and a probe to detect a nucleic acid of an arbovirus. In other embodiments, the methods provide using more than one primer and a probe to detect a nucleic acid of an arbovirus. In some embodiments, the nucleic acid of one arbovirus is detected in a single sample. In some embodiments, the nucleic acid of more than one arbovirus is detected in a single sample.

One method of detecting a nucleic acid of an arbovirus generally comprises contacting a primer hybridized to a nucleic acid of the virus with an enzyme with 5' nuclease activity. The enzyme with 5' nuclease activity then fragments a probe hybridized to the nucleic acid of the virus in a 5' nuclease reaction. The probe can be labeled with a detectable moiety that enables detection of fragmentation of the probe. Such methods are based on those described in U.S. Pat. Nos. 6,214,979, 5,804,375, 5,487,972 and 5,210,015.

In a 5' nuclease reaction, the nucleic acid, primer and probe can be contacted with any enzyme known by one of skill in the art to have 5' to 3' nuclease activity without limitation. The conditions are preferably chosen to permit the polymerase to cleave the probe and release a plurality of fragments of the probe from the nucleic acid. Preferred enzymes with 5' nuclease activity include template-dependent nucleic acid polymerases. Known native and recombinant forms of such polymerases include, for example, *E. coli* DNA polymerase I (Fermentas, Inc., Hanover, Md.), *Bacillus stearothermophilus* DNA polymerase, and *Thermococcus littoralis* DNA polymerase.

In preferred embodiments, the enzymes with 5' nuclease activity are thermostable and thermoactive nucleic acid polymerases. Such thermostable polymerases include, but are not limited to, native and recombinant forms of polymerases from a variety of species of the eubacterial genera *Thermus, Thermatoga*, and *Thermosipho*.

A 5' nuclease reaction comprises contacting the nucleic acid to be detected with a primer, a probe, and an enzyme having 5' to 3' nuclease activity, under conditions in which the primer and the probe hybridize to the nucleic acid. Components of a 5' nuclease reaction can contact the nucleic acid to be detected in any order, e.g., the primer can contact the nucleic acid to be detected first, followed by the probe and enzyme with 5' nuclease activity, or alternatively the enzyme with 5' nuclease activity can contact the nucleic acid to be detected first, followed by the probe and primer. In certain embodiments, more than one primer or probe may be added to a 5' nuclease reaction. In certain preferred embodiments, a pair of primers can contact the nucleic acid in a 5' nuclease reaction. The primer can be any primer capable of priming a DNA synthesis reaction. Where only one primer is used, the primer should hybridize to the nucleic acid upstream of the probe, i.e., the 3' end of the primer should point toward the 5' end of the probe. The 3' end of the primer can hybridize adjacent to the 5' end of the probe, or the 3' end of the primer can hybridize further upstream of the 5' end of the probe. Where more than one primer is used, at least one primer should hybridize to the nucleic acid to be detected upstream of the probe, as described above.

Certain embodiments of the 5' nuclease reactions of the present invention are based on several 5' nuclease reactions that are known to those of skill in the art. Examples of such reactions are described in detail, for instance, in U.S. Pat. No. 5,210,015.

Briefly, in a 5' nuclease reaction, a target nucleic acid is contacted with a primer and a probe under conditions in which the primer and probe hybridize to a strand of the nucleic acid. The nucleic acid, primer and probe are also contacted with an enzyme, for example a nucleic acid polymerase, having 5' to 3' nuclease activity. Nucleic acid polymerases possessing 5' to 3' nuclease activity can cleave the probe hybridized to the nucleic acid downstream of the primer. The 3' end of the primer provides a substrate for extension of a new nucleic acid as based upon the template nucleic acid by the nucleic acid polymerase. As the polymerase extends the new nucleic acid, it encounters the 5' end of the probe and begins to cleave fragments from the probe.

The primer and probe can be designed such that they hybridize to the target nucleic acid in close proximity to each other such that binding of the nucleic acid polymerase to the 3' end of the primer puts it in contact with the 5' end of the probe. In this process, nucleic acid extension is not required to bring the nucleic acid polymerase into position to accomplish the cleavage. The term "polymerization-independent cleavage" refers to this process.

Alternatively, if the primer and probe anneal to more distantly spaced regions of the nucleic acid, nucleic acid extension must occur before the nucleic acid polymerase encounters the 5' end of the probe. As the polymerization continues, the polymerase progressively cleaves fragments from the 5' end of the probe. This cleaving continues until the remainder of the probe has been destabilized to the extent that it dissociates from the template molecule. The term "polymerization-dependent cleavage" refers to this process.

In either process, a sample is provided which contains the nucleic acid. If the nucleic acid is double-stranded, it should first be denatured, e.g., the strands of the nucleic acid separated from each other. Any suitable denaturing method, including physical, chemical, or enzymatic means, known to one of skill in the art without limitation can be used to separate the nucleic acid strands.

It should be noted that the viruses that can be detected with the primers, probes, methods, and kits of the invention are single stranded plus-strand RNA viruses. Accordingly, denaturation of the native viral genome is not required to detect an unamplified viral genome. However, if the native viral genome is reverse-transcribed into DNA according to certain embodiments of the invention, denaturation of the amplified viral nucleic acids is necessary prior to detection with the primers and probes of the invention.

If the nucleic acid to be detected is RNA, the RNA can either be used as an RNA template for a 5' nuclease reaction as described above, or the RNA can be used as a template for reverse-transcription into cDNA, or both simultaneously. In certain embodiments, the RNA can be detected without reverse-transcription into cDNA using the methods of the invention. Polymerization-independent cleavage methods as described above are particularly well-suited for such embodiments. In other embodiments, the RNA can be first reverse-transcribed into cDNA in the absence of a probe, and then the cDNA product can be detected according to the methods of the invention. In still other embodiments, the RNA can be reverse-transcribed in the presence of a probe, simultaneously producing cDNA that can subsequently be amplified and/or detected and detecting the presence of the RNA by assessing fragmentation of the probe as described herein.

Where the RNA is reverse-transcribed in the absence of a probe, the RNA can be reverse transcribed into cDNA by any method known to one of skill in the art. The products of such reverse transcription can then be detected like any detectable nucleic acid according to the methods described herein.

Where the RNA is reverse-transcribed in the presence of a probe, the RNA can be reverse-transcribed by a DNA polymerase with 5'-3' nuclease activity that can use RNA as a template for DNA strand synthesis. As with all known DNA polymerase synthesis activities, such synthesis requires the presence of a primer, such as those described herein. The DNA polymerase that can use RNA is a template is preferably thermostable, so that multiple cycles of denaturation and DNA synthesis can occur without destroying the polymerase. Further, the DNA polymerase used for reverse transcription can preferably also synthesize DNA using a DNA template. Such polymerases are described in, for example, U.S. Pat. No. 6,468,775 (*Carboxydothermus hydrogenformans* DNA polymerase), U.S. Pat. No. 5,968,799 (*Thermosipho africanus* DNA polymerase), U.S. Pat. No. 5,736,373 (*Bacillus pallidus* DNA polymerase), U.S. Pat. No. 5,674,738 (*Thermus* species Z05 DNA polymerase), and U.S. Pat. No. 5,407,800 (*Thermus aquaticus* and *Thermus thermophilus* DNA polymerases). In addition, methods and compositions for reverse transcribing an RNA using a thermostable DNA polymerase with reverse transcription activity are described in U.S. Pat. Nos. 5,693,517, 5,561,058, 5,405,774, 5,352,600, 5,310,652, and 5,079,352.

Whether RNA or DNA, the denatured nucleic acid strand is then contacted with a primer and a probe under hybridization conditions, which enable the primer and probe to bind to the nucleic acid strand. In certain embodiments, two primers can be used to amplify the nucleic acid. In such embodiments, the two primers can be selected so that their relative positions along the nucleic acid are such that an extension product synthesized from one primer, after the extension produce is separated from its template (complement), can serve as a template for the extension of the other primer to yield an amplified product of defined length. The length of the product depends on the length of the sequence between the two primers and the length of the two primers themselves.

The probe preferably hybridizes to the nucleic acid to be detected before the polymerase binds the nucleic acid and primer and begins to extend the new nucleic acid strand from the primer based upon the template of the detectable nucleic acid. It is possible for the polymerase to bind the primer and nucleic acid to be detected before the probe contacts the detectable nucleic acid; however, this arrangement can result in decreased probe fragmentation unless multiple cycles of primer extension are performed, as in a preferred PCR based 5' nuclease reaction as described below. Accordingly, it is preferable that the probe hybridize to the nucleic acid to be detected before primer extension by the polymerase begins.

A variety of techniques known to one of skill in the art can be employed to enhance the likelihood that the probe will hybridize to the detectable nucleic acid before primer extension polymerization reaches this duplex region, or before the polymerase attaches to the upstream oligonucleotide in the polymerization-independent process. For example, short primer molecules generally require cooler temperature to form sufficiently stable hybrid complexes with the nucleic acid. Therefore, the probe can be designed to be longer than the primer so that the probe anneals preferentially to the nucleic acid at higher temperatures relative to primer annealing.

One can also use primers and probes having differential thermal stability based upon their nucleotide composition. For example, the probe can be chosen to have greater G/C content and, consequently, greater thermal stability than the primer. Alternatively or additionally, one or more modified, non-standard or derivatized DNA bases may be incorporated into primers or probes to result in either greater or lesser thermal stability in comparison to primers or probes having only conventional DNA bases. Examples of such modified, non-standard or derivatized bases may be found in U.S. Pat. Nos. 6,320,005, 6,174,998, 6,001,611, and 5,990,303.

Further, the temperature of the reaction can also be varied to take advantage of the differential thermal stability of the probe and primer. For example, following denaturation at high temperatures as described above, the reaction can be incubated at an intermediate temperature which permits probe but not primer binding, followed by a further temperature reduction to permit primer annealing and subsequent extension.

Template-dependent extension of the oligonucleotide primer(s) is catalyzed by a DNA polymerase in the presence of adequate amounts of the four deoxyribonucleoside triphosphates (dATP, dGTP, dCTP, and dTTP) or analogs, e.g., dUTP, as discussed above, in a reaction medium which is comprised of the appropriate salts, metal cations, and pH buffering system. Suitable polymerizing agents are enzymes known to catalyze primer and template-dependent DNA synthesis and possess the 5' to 3' nuclease activity. Such enzymes include, for example, *Escherichia coli* DNA polymerase I, *Thermus thermophilus* DNA polymerase, *Bacillus stearothermophilus* DNA polymerase, *Thermococcus littoralis* DNA polymerase, *Thermus aquaticus* DNA polymerase, *Thermatoga maritima* DNA polymerase and *Thermatoga neapolitana* DNA polymerase and Z05 DNA polymerase. Further, the reaction conditions for performing DNA synthesis using these DNA polymerases are well known in the art. To be useful in the methods of the present invention, the polymerizing agent should possess 5' nuclease activity that can efficiently cleave the oligonucleotide and release labeled fragments so that a detectable signal is directly or indirectly generated.

The products of the synthesis are duplex molecules consisting of the template strands and the primer extension strands. Byproducts of this synthesis are probe fragments which can consist of a mixture of mono-, di- and oligonucleotide fragments. In preferred embodiments, repeated cycles of denaturation, probe and primer annealing, and primer extension and cleavage of the probe can be performed, resulting in exponential accumulation of the amplified region defined by the primers and exponential generation of labeled fragments. Such repeated thermal cycling is generally known in the art as the polymerase chain reaction (PCR). Sufficient cycles can be performed to achieve fragment a sufficient amount of the probe to distinguish positive reactions, i.e., the nucleic acid to be detected is present, from negative reactions, i.e., the nucleic acid to be detected is not present. Generally, positive reactions will exhibit a signal that is several orders of magnitude greater than a negative reaction.

In certain preferred embodiments, the PCR reaction is carried out as an automated process which utilizes a thermostable enzyme. In this process the reaction mixture is cycled through a denaturing step, a probe and primer annealing step, and a synthesis step, whereby cleavage and displacement occur simultaneously with primer dependent template extension. In certain of such embodiments of the invention, the nucleic acids to be detected can be amplified in the absence of a detectably-labeled probe, followed by detection of the amplification product in a separate reaction. Alternatively, the nucleic acids to be detected can be amplified in the presence of the probe, allowing amplification and detection in a single reaction.

Temperature stable polymerases are preferred in this automated process because the preferred way of denaturing the double stranded extension products is by exposing them to a high temperature during the PCR cycle. For example, U.S. Pat. No. 4,889,818 discloses a representative thermostable enzyme isolated from *Thermus aquaticus*. Additional representative temperature stable polymerases include, e.g., polymerases extracted from the thermostable bacteria *Thermus flavus, Thermus Tuber, Thermus thermophilus, Bacillus stearothermophilus* (which has a somewhat lower temperature optimum than the others listed), *Thermus lacteus, Thermus rubens, Thermotoga maritima, Thermococcus littoralis, Methanothermus fervidus,* and *Pyrococcus furiosus* (Stratagene, La Jolla, Calif.). As described above, certain of these thermostable polymerases can synthesize DNA from an RNA template. Where an RNA molecule is to be detected according to the methods of the invention, a DNA polymerase that can synthesize DNA from an RNA template, i.e., with reverse transcription activity, should be used.

The primer and probes described herein can be used in methods and systems utilizing a PCR format including those described above, many of which are commercially available and in an automated system. Exemplified herein is an assay denoted CII-ArboPlex rRT-PCR which utilizes SEQ ID NOs: 1-13 as well as controls SEQ ID NOs: 14-16. See Example 1 and Table 2. In the exemplified assay, dual-labeled BHQ probes are used which are linear, dual labeled 5'-3' exonuclease probes incorporating a fluorophore and quencher covalently attached to the 5' and 3' ends of the oligonucleotide, respectively. Fluorescence signal is generated through the 5' exonuclease activity of Taq polymerase, which cleaves off the fluorescent dye-labeled nucleotide from the probe during digestion of the probe hybridized to its complementary sequence in the target strand and thus separating quencher from fluorophore. The five primer and probe sets were designed to detect RNA from the ZIKV, DENV, CHIKV, WNV and RNase P in serum and urine from patients presenting with signs and symptoms of the respective virus infection and/or epidemiological risk factors consistent with viral exposure. After patient specimen collection and receipt by the laboratory, total nucleic acids can be isolated from samples using the NucliSENS® easyMag® automated extraction platform (bioMérieux). The purified nucleic acids can be reverse transcribed and amplified by using the RNA UltraSense™ One-Step Quantitative RT-PCR System (ThermoFisher) with thermal cycling and detection on the CFX96 Touch™ Real-Time PCR Detection System (Bio-Rad). In the process, the specific probe anneals to a specific target sequence located between the specific forward and reverse primers generating a fluorescent signal, which is measured during the end of the elongation phase of the PCR cycle. With each cycle of PCR, more probes are digested, resulting in an increase in fluorescence that is proportional to the amount of target nucleic acid. Fluorescence signal intensity is analyzed and data collected by the CFX Manage™ Software. See Examples 1-4. Results of the assay are analyzed as set forth in Example 5.

In particular, an up to 58-samples/day, from clinical specimen extraction to result, can be evaluated for ZIKV, DENV (serotypes 1-4), CHIKV and WNV using a single bioMérieux NucliSENS® easyMag® and a CFX96 Touch™ Real-Time PCR Detection platform (Bio-Rad) and the assay of the invention. The time required to extract 58 samples is about 60 minutes times 3 runs equals about 3 hours and the time required to set up and perform CII-ArboPlex rRT-PCR assay is about 2 hours, making the total time required to be about 5 hours to test one 96-well plate representing 29 specimens per instrument run.

Using the exemplified assay and the primers and probes SEQ ID NOs: 1-13, the sensitivity, specificity, and cross-reactivity of the assay was evaluated and it was determined that the assay performed as required to differentially detect the arboviruses, including ZIKV, DENV, CHIKV, and WNV in both serum and urine. See Examples 6-9. Additionally, the performance characteristics of the assay using clinical samples (both serum and urine) known to be positive or negative for particular viruses was also evaluated and found to perform as required. See Examples 10-13.

The present invention includes methods and systems for the detection of nucleic acid from ZIKV, DENV, CHIKV, and WNV in any sample utilizing the primers and probes of the present invention.

The methods and systems of the present invention may be used to detect nucleic acids from ZIKV, DENV, CHIKV, and WNV in research and clinical settings.

A preferred sample is a biological sample. A biological sample may be obtained from a tissue of a subject or bodily fluid from a subject including but not limited to nasopharyngeal aspirate, blood, cerebrospinal fluid, saliva, serum, plasma, urine, sputum, bronchial lavage, pericardial fluid, or peritoneal fluid, or a solid such as feces. The preferred sample is serum, plasma and urine. The subject may be any animal, particularly a vertebrate and more particularly a mammal, including, without limitation, a cow, dog, human, monkey, mouse, pig, or rat. In one embodiment, the subject is a human.

A sample may also be a research, clinical, or environmental sample.

Additional applications include, without limitation, detection of the screening of blood products (e.g., screening blood products for infectious agents), biodefense, food safety, environmental contamination, forensics, and genetic-comparability studies. The present invention also provides methods and systems for detecting viral nucleic acids in cells, cell culture, cell culture medium and other compositions used for the development of pharmaceutical and therapeutic agents.

Thus, one embodiment of the present invention provides a system for the detection of nucleic acid from ZIKV, DENV, CHIKV, and WNV, or of detection of the virus itself, in any sample. The system includes at least one subsystem wherein the subsystem includes: the primer groups comprising SEQ ID NOs: 1 and 2; SEQ ID NOs: 4 and 5; SEQ ID NOs: 7, 8, and 9; and SEQ ID NOs: 11 and 12; and probes comprising SEQ ID NOs: 3, 6, 10, and 13. The system can also include additional subsystems for the purpose of: extraction of nucleic acids from the sample; reverse transcribing the nucleic acid from the sample; amplifying the reaction; and detection of the amplification products.

The present invention provides a method for detecting nucleic acid from ZIKV, DENV, CHIKV, and WNV, or of detection of the virus itself, in any sample, including the steps of: obtaining the sample; extracting nucleic acid from the sample; contacting the nucleic acid in the sample with at least one primer selected from the group consisting of SEQ ID NOs: 1, 2, 4, 5, 8, 9, 10, 11, and 12; subjecting the nucleic acid and primer to amplification conditions; and detecting the presence of amplification product, wherein the presence of the amplification products indicates the presence of nucleic acid of the virus in the sample.

In one embodiment, the method comprises contacting the nucleic acid from the sample with primer groups comprising SEQ ID NOs: 1 and 2; SEQ ID NOs: 4 and 5; SEQ ID NOs: 7, 8, and 9; and SEQ ID NOs: 11 and 12. In a further embodiment, the method comprises further contacting the nucleic acid from the sample with probes comprising SEQ ID NOs: 3, 6, 10, and 13. In yet a further embodiment, the probes are detectable in order to detect the presence of the amplification product in the sample.

Kits

In another aspect, the present invention provides kits that can be used to detect a nucleic acid of an arbovirus or the arbovirus itself. The kit can be used to detect nucleic acid from Zika, dengue, chikungunya, and West Nile viruses and/or the detection of the Zika, dengue, chikungunya, and West Nile virus. In certain embodiments, the kit comprises a probe of the invention. In some embodiments, the kit comprises a primer of the invention. In some embodiments, the kit comprises a combination of one or more of the primers and probes of the invention.

In certain embodiments, the kit comprises a combination of one or more of the primers and probes of the invention. In certain embodiments the kit comprises one or more primers chosen from the group consisting of SEQ ID NOs: 1, 2, 4, 5, 7, 8, 9, 11, and 12. In certain embodiments, the kit comprises one or more probes chosen from the group consisting of SEQ ID NOs: 3, 6, 10, and 13. In certain embodiments, the kit further comprises primers and probes for positive control sequences. In certain embodiments, the kit further comprises primers and probes for detecting human RNase. In certain embodiments, the kit comprises primers and probe comprising SEQ ID NOs: 14-15.

In certain embodiments, the kits of the invention comprise an oligonucleotide useful as a nucleic acid probe, wherein one or more detectable moieties are attached to the nucleic acid probe. In certain embodiments, the one or more detectable moieties are a fluorescent moiety. In certain embodiments, the fluorescent moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes.

In certain embodiments, the kits of the invention comprise an oligonucleotide useful as a nucleic acid probe, wherein at least one quencher moiety is attached to the nucleic acid probe. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQT™-family dyes, Iowa Black™, or Dabcyl. In other embodiments, the probe comprises at least one detectable moiety, e.g. a fluorescent moiety and at least one quencher moiety.

In certain embodiments, the kits of invention comprise a thermostable DNA polymerase. In certain embodiments, the thermostable DNA polymerase has reverse transcription activity. In certain embodiments, the kits of the invention additionally comprise instructions for detecting a nucleic acid of Zika, dengue, chikungunya, and West Nile according to the methods of the invention In other embodiments, the kits comprise one or more containers to hold the components of the kit.

In certain embodiments, the kits can contain a composition comprising a primer of the invention. The kits can also contain a composition comprising a probe of the invention. The kits can further contain a composition comprising a thermostable DNA polymerase. In some embodiments, the thermostable DNA polymerase is selected from the group of *Carboxydothermus hydrogenformans* DNA polymerase, *Thermosipho africanus* DNA polymerase, *Bacillus pallidus* DNA polymerase, *Thermus* species Z05 DNA polymerase, *Thermus aquaticus* DNA polymerase, *Thermus thermophilus* DNA polymerase, *Thermatoga maritima* DNA polymerase, *Thermatoga neapolitana* DNA polymerase and *Thermus* sps17 DNA polymerase The compositions comprising a primer or probe of the invention or a thermostable DNA polymerase can further comprise additional reagents. For example, the compositions can comprise suitable preservatives prevent degradation of the composition, suitable buffers to modulate the pH of the composition, suitable diluents to alter the viscosity of the compositions, and the like.

The kits can additionally comprise other reagents for carrying out a 5' nuclease reactions, as described above. In addition, the kits can comprise reagents to facilitate the detection of a fragmented probe that indicates the presence of a nucleic acid of ZIKV, WNV, DENV, and CHIKV.

In certain embodiments of the invention, the kits includes 5 vials with primers and probe for each target combined in each vial, 4 vials containing extracted nucleic acid of each viral agent as positive controls (measured), two vials of human specimen control (HSC) used as extraction control and rRT-PCR control (virus negative, RNase P positive) and two vials sterile distilled H₂O used as non-template control (NTC) and provides sufficient reagents for 100 reactions.

One embodiment of the present invention is a kit comprising various containers comprising various components for the differential detection of Zika, dengue, chikungunya, and West Nile viruses in a single sample, as described in Table 1.

TABLE 1

| | Kit Reagents | |
|---|---|---|
| | Vial Label | Vial component |
| 1 | ZIKV-MIX | ZIKV forward primer (SEQ ID NO: 1) |
| | | ZIKV reverse primer (SEQ ID NO: 2) |
| | | ZIKV probe (SEQ ID NO: 3) |
| 2 | WNV-MIX | WNV forward primer (SEQ ID NO: 4) |
| | | WNV reverse primer (SEQ ID NO: 5) |
| | | WNV probe (SEQ ID NO: 6) |
| 3 | DENV-MIX | DENV forward primer (SEQ ID NO: 7) |
| | | DENV reverse primer A (SEQ ID NO: 8) |
| | | DENV reverse primer B (SEQ ID NO: 9) |
| | | DENV probe (SEQ ID NO: 10) |
| 3 | CHIKV-MIX | CHIKV forward primer (SEQ ID NO: 11) |
| | | CHIKV reverse primer (SEQ ID NO: 12) |
| | | CHIKV probe (SEQ ID NO: 13) |
| 5 | RP-MIX | RNase P forward primer (SEQ ID NO: 14) |
| | | RNase P reverse primer (SEQ ID NO: 15) |
| | | RNase P probe (SEQ ID NO: 16) |
| 6 | ZPC | ZIKV Positive Control |
| 7 | WPC | WNV Positive Control |
| 8 | DPC | DENV Positive Control |
| 9 | CPC | CHIKV Positive Control |
| 10 | HSC | Human specimen extraction control (HSC) |
| 11 | eHSC | Extracted nucleic acid from HSC |
| 11 | NTC | Distilled water negative control |

In preferred embodiments, the probes comprise a detectable moiety. In a more preferred embodiment, the probe for the detection of Zika virus, SEQ ID NO: 3, is modified at 5' with CAL Fluor Red 610 and 3' with BHQ-2; the probe for the detection of West Nile Virus, SEQ ID NO: 7, is modified at 5' with Quasar 670 and 3' with BHQ-2; the probe for the detection of dengue virus, SEQ ID NO: 11, is modified 5' with CAL Fluour Orange 56 and 3' with BHQ-1 plus; and the probe for detection of chikungunya virus, SEQ ID NO: 14, is modified 5' with FAM and 3' with BHQ-1 plus. The probe for detection of RNASE-P, SEQ ID NO: 16, is modified 5' with Quasar 705 and 3' with BHQ-3.

In one embodiment, the kit provides positive, negative and HSC extraction controls and instructions regarding the expected results.

In one embodiment, positive controls (vials 6-9) comprise extracted nucleic acid from infected culture cells. The RNA positive controls for ZIKV, WNV, DENV and CHIKV should be positive within the expected Ct value range (25-28).

The human specimen control (HSC) (vial 10) of the kit provides a human extraction control that is extracted concurrently with the test samples and included as a sample during rRT-PCR. The HSC should generate negative results for ZIKV, DENV, CHIKV and WNV primer and probe sets, but positive results for RNase P. If no RNase P signal is recorded, the nucleic acid extraction may have failed. A positive assay for RNase P and one or more virus primer/probe sets indicates cross-contamination. If such a result is obtained, disregard all specimen results.

The kit also provides a rRT-PCR control (eHSC) (vial 11), which is extracted nucleic acid from the human specimen control (HSC), and a negative control, (NTC) (vial 12)which is sterile nuclease free H₂O for NTCs. NTCs should be negative. Positive NTCs indicate contamination and all specimen results must be disregarded; and RNase P-results for each specimen should be positive to confirm successful extraction of nucleic acid from sample specimen. Results for samples with no RNase P signal detected must be disregarded.

Additional components of this kit could include a thermostable DNA polymerase with reverse transcription activity, stabilizers, ribonuclease inhibitors, buffers, and instructions.

EXAMPLES

The present invention may be better understood by reference to the following non-limiting examples, which are presented in order to more fully illustrate the preferred embodiments of the invention. They should in no way be construed to limit the broad scope of the invention.

Example 1—Primers and Probes for Use in the Assay

The following probes and primers were used in the Examples.

TABLE 2

Primers and Probes

| Primer/Probe Gene Name | Probe modification | Sequence (5' to 3') | SEQ ID NO: |
|---|---|---|---|
| ZIKA.3P.QF | | ARTGTTGTCAGGCCTGCTAG | 1 |
| ZIKA.3P.QR | | CTTGRTTTCCCAGCKTCTCCT | 2 |
| ZIKA.3P.Probe.R610 | CAL Fluor Red 610 (5'); Bhq (3') | GGGGAAAGCTGTGCAGCCTGT | 3 |
| WNV.NS5.NQF | | CATTTGCTCCGCTGTCCCTGTGAA | 4 |
| WNV.NS5.NQR | | CCACTCTCCTCCTGCATGGATGGAC | 5 |
| WNV.NS5.Probe.Q670 | Quasar 670 (5'); BHQ-2 (3') | TGGGTCCCTACCGGAAGAACCACGT | 6 |
| DENV.3P.QF | | ACTAGAGGTTAGAGGAGACCCCC | 7 |
| DENV.3P.QRA | | GGCGCTCTGTGCCTGGATT | 8 |
| DENV.3P.QRB | | TGGCGTTCTGTGCCTGGAAT | 9 |
| DENV.3P.Probe.O560 | CAL Fluor Orange 560 (5'); BHQ-1 Plus (3') | CCCAGCGTCAATATGCTGT | 10 |
| CHIK.NSP2.NQF | | CATCTGCACYCAAGTGTACCA | 11 |
| CHIK.NSP2.NQR | | GCGCATTTTGCCTTCGTAATG | 12 |
| CHIK.NSP2.Probe.FAM | FAM (5'); BHQ-1 plus (3') | AAAAGTATCTCCAGGCGG | 13 |
| RNASE-P-QF | | AGATTTGGACCTGCGAGCG | 14 |
| RNASE-P-QR | | GAGCGGCTGTCTCCACAAG | 15 |
| RNASE-P-Probe.Q705 | Qusar 705 (5'); BHQ-3 (3') | TCTGACCTGAAGGCTCTGCGCG | 16 |

All of the primers and probes are universal. The Zika primers and probes target the 3'UTR of the ZIKV genomic RNA (SEQ ID NOs: 1-3). The West Nile Virus primers and probe target the NS5 gene of the WNV genomic RNA (SEQ ID NOs; 4-6). The dengue virus primers and probe target the 3'UTR of the DENV genomic RNA (SEQ ID NOs: 7-10). The gene target of the Chikungunya virus primers and probe is the NSP2 gene of the CHIKV genomic RNA (SEQ ID NOs; 11-13).

SEQ ID NOs: 14-16 are control primers and probe. The gene target is human ribonuclease P subunit p30 mRNA.

Example 2—Reagents and Materials for the Multiplex Assay

The probes and primers listed in Table 2 were provided in one vial for each virus in lyophilized form to be reconstituted in 100 μl of H$_2$O. The vial labeled ZIKV-MIX contained primers and probe SEQ ID NOs: 1-3. The vial labeled WNV-MIX contained primers and probe SEQ ID NOs: 4-6. The vial labeled DENV-MIX contained primers and probe SEQ ID NOs: 7-10. The vial labeled CHIK-MIX contained primers and probe SEQ ID NOs; 11-13. The vial labeled RP-MIX contained primers and probe SEQ ID NOs: 14-16. See Tables 1 and 2.

Additional reagents included assay controls in the labeled vials as set forth in Tables 1 and 3.

All the assay controls should be included in each plate and tested concurrently with clinical samples. These assay controls include extractions control reagents, positive control for each virus, and others.

The extraction control is a human specimen control (HSC, extraction control) and is a human culture cell extract known to contain RNase P template but that is negative for the investigated viral targets. The HSC control is included with each batch of test specimens and concurrently extracted. The extracted HSC control nucleic acid can be included with its concurrently extracted test samples on each PCR plate and analyzed by rRT-PCR.

The HSC control should generate negative results for DENV, CHIKV, WNV and ZIKV (no fluorescence signal from the respective probes/dyes), but a positive result should be obtained for RNase P (fluorescence signal for Quasar 705 dye).

The positive controls for viruses should be positive for only one virus. The following positive controls should be tested on each PCR plate:

ZIKV Positive Control: Extracted nucleic acid from ZIKV infected culture cells is used as a control for performance of ZIKV primer/probe set and PCR reagent function.

CHIKV Positive Control: Extracted nucleic acid from CHIKV infected cultured cells is used as a control for performance of ZIKV primer/probe set and PCR reagent function.

WNV Positive Control: Extracted nucleic acid from WNV infected cultured cells is used as a control for performance of ZIKV primer/probe set and PCR reagent function.

DENV Positive Control: Extracted nucleic acid from DENV-1 infected cultured cells is used as a control for performance of ZIKV primer/probe set and PCR reagent function.

Other controls include a No Template Controls (NTC) and a RT-PCR Control (eHSC). Two no template controls (NTC; sterile, nuclease-free water) can be run on each PCR plate. Extracted nucleic acid from human culture cells (eHSC) known to contain RNase P is used as a control for RNA integrity and the absence of rRT-PCR inhibitors.

These reagents and amounts in each vial for the assay are listed in Table 3.

TABLE 3

Additional Components of the Assay

| ZPC | ZIKV Positive Control | 1 | 30 μl |
|---|---|---|---|
| WPC | WNV Positive Control | 1 | 30 μl |
| DPC | DENV Positive Control | 1 | 30 μl |
| CPC | CHIKV Positive Control | 1 | 30 μl |
| HSC | Human specimen extraction control (HSC) | 2 | 1.5 ml per each vial |
| eHSC | Extracted nucleic acid from HSC | 1 | 30 μl |
| NTC | Distilled water negative control | 2 | 750 μl in each vial |

Additional reagents and materials and equipment that were used in the method and assay include those for nucleic acid isolation from a sample used in the NucliSENS® easyMag® automated total nucleic acid extraction method and include NucliSENS® easyMag® Magnetic Silica (bioMérieux catalog #280133); NucliSENS® easyMag® Disposables (bioMérieux catalog #280135); NucliSENS® easyMag® Buffer 1 (bioMérieux catalog #280130); NucliSENS® easyMag® Buffer 2 (bioMérieux catalog #280131); NucliSENS® easyMag® Buffer 3 (bioMérieux catalog #280132); and NucliSENS® easyMag® Lysis Buffer (bioMérieux catalog #280134) as well as the bioMérieux NucliSENS® easyMag® system (bioMérieux; catalog #280140).

Additional reagents and materials that were used in the method and assay include those for polymerase chain reaction including molecular-grade water, nuclease-free and RNA UltraSense™ One-Step Quantitative RT-PCR System (ThermoFisher Scientific, catalog #11732927) as well as the CFX96 Touch™ Real-Time PCR Detection System (Bio-Rad).

The nucleic acid extraction and polymerase chain reaction were performed following manufacturer's instructions.

Example 3—Nucleic Acid Extraction and Storage

Manufacturer's instructions for NucliSENS® easyMag® were generally followed for the extraction process and machine interface operation.

Briefly a specimen input volume of 250 μL and an elution volume of 50 μL total nucleic acid was used.

Biological samples including urine and serum that are previously collected and frozen are thawed on ice. A 250 μL sample is pipetted and mixed with 750 μL NucliSENS® easyMag® Lysis Buffer and incubated for 10-15 minutes at room temperature (The standard ratio is 1:3 sample to lysis buffer).

50 μL NucliSENS® easyMag® Magnetic Silica beads was added to the sample+lysis buffer mix and mixed thoroughly by pipetting up and down of the sample and magnetic silica beads. The samples were transferred into a NucliSENS® easyMag® sample cartridge. The magnetic silica cartridge was loaded into the machine along with the pipette cartridge and the sample processed.

When the run was completed, the 50 μL of eluted total nucleic acid is transferred into a clean reaction tube for PCR assay setup. Alternatively, the sample is stored at ≤−70° C.

Example 4—rRT-PCR Assay Set Up

A master mix was made using the following components. For more than one reaction the recipe should be modified accordingly.

TABLE 4

Master Mix Components for rRT-PCR

| Assay Components | Volume per reaction (μl) |
|---|---|
| RNA UltraSense ™ 5X Reaction Mix | 5 |
| RNA UltraSense ™ Enzyme Mix* | 1.25 |
| CHIKV-MIX# | 1 |
| DENV-MIX# | 1 |
| ZIKV-MIX# | 1 |
| WNV-MIX# | 1 |
| RP-MIX# | 1 |
| $H_2O$ | 3.75 |
| Template (TNA/RNA) | 10 |
| Total reaction volume | 25 |

The master mix was aliquoted into wells of PCR platform. Each run should include all of the controls described in Example 2 including positive controls for CHIKV, ZIKV, DENV, WNV, human extraction control (HSC), rRT-PCR control (extracted HSC control; eHSC) and 3 negative no template controls (NTC) (Table 3). Samples are tested in triplicate.

The specimens were run on a CFX96 Touch™ real time PCR detection platform, programmed according to manufacturer's instructions for multiplex detection selecting dye channels FAM, Cal Orange 560, Cal Red 610, Quasar 670, and Quasar 705 and the following cycling profile and dye selections with the following cycling protocol.
1. 50.0° C. for 30 minutes
2. 95.0° C. for 2 minutes
3. 95.0° C. for 15 seconds
4. 60.0° C. for 1 minute
+Plate Read
5. Go to step 3 for 44 times
6. End

Example 5—Interpretation of Results and Examination of Patient Specimen Results All data from test controls should be examined prior to interpretation of patient results. If the controls are not valid, the patient results cannot be interpreted. Each assay should be performed with proper positive and negative controls. CII-ArboPlex rRT-PCR assay provides positive, negative and HSC extraction controls. All the controls must yield the expected results:

Human specimen control (HSC)—The CII-ArboPlex rRT-PCR assay kit provides a human extraction control that is extracted concurrently with the test samples and included as a sample during rRT-PCR. The HSC should generate negative results for ZIKV, DENV, CHIKV and WNV primer and probe sets, but positive results for RNase P. If no RNase P signal is recorded, the nucleic acid extraction may have failed (see also 'rRT-PCR control' and 'RNase P' below). A positive assay for RNase P and one or more virus primer/probe sets indicates cross-contamination. If such a result is obtained, disregard all specimen results.

rRT-PCR control (eHSC)—Extracted nucleic acid from human specimen control (HSC).

Positive Controls—The CII-ArboPlex rRT-PCR assay kit provides extracted RNA positive controls for ZIKV, WNV, DENV and CHIKV that should be positive within the expected Ct value range (25-28). Repeat the rRT-PCR if one or more positive controls yield negative results, or increased Ct values (Ct>31).

NTCs—The CII-ArboPlex rRT-PCR kit provides sterile nuclease free $H_2O$ for NTCs. NTCs should be negative. Positive NTCs indicate contamination and all specimen results must be disregarded.

RNase P-Results for each specimen should be positive to confirm successful extraction of nucleic acid from sample specimen. Results for samples with no RNase P signal detected must be disregarded. Repeat extraction from new specimen aliquot. If RNase P is positive report virus specific result(s), if RNase P is still negative no results can be reported.

Assessment of clinical specimen test results should be performed after the positive and negative controls have been examined and determined to be valid and acceptable. If the controls are not valid, the patient results may not be interpreted. If a PCR amplification curve, based on increasing fluorescence emission for a primer probe set crosses the threshold within ($\leq$) 38 cycles the result is positive, if the amplification curve for a primer probe set crosses the threshold at or above ($\geq$) 38 cycles the result is negative. FIG. 1 sets forth the interpretation of clinical specimen results.

The users can follow CII-ArboPlex rRT-PCR results interpretation and reporting instructions (FIG. 1). All controls should yield the expected results for further analysis of specimen data. True positives should produce exponential curves with Ct values $\leq$38. Samples that do not show exponential amplification or do not cross the threshold in 38 or less cycles are considered negative. If two of the three test wells are positive, the result for the sample is positive; if two of three wells are negative, the result for the sample is negative.

Example 6—Analytical Sensitivity Assessment of the Assay in Serum

Using the materials and methods set forth in Examples 1-5 and the virus stocks described in Table 5, the analytical sensitivity of the assay was tested in serum.

Viral copy numbers (genomic equivalent quantities, GEQ/ml) were estimated for each virus using serial dilutions of synthetic T7 in vitro transcribed RNA transcripts that were calibrated for each target.

TABLE 5

Viral Stocks Used in Analytical Sensitivity Tests

| Virus Stock | Sample type | Cell line | Strain | Virus stock TCID50 (U/mL) | Copy Number (GEQ/ml) |
|---|---|---|---|---|---|
| Zika virus | Virus culture supernatant | Vero | PRVABC59 | $6.61 \times 10^{*6}$ | $5.16 \times 10^{*7}$ |
| Chikungunya Virus | Virus culture supernatant | Vero | R80422 | $3.56 \times 10^{*6}$ | $5.39 \times 10^{*7}$ |
| Dengue Virus Type 1 | Virus culture supernatant | Vero | Hawaii | $1.70 \times 10^{*5}$ | $4.37 \times 10^{*6}$ |
| Dengue Virus Type 2 | Virus culture supernatant | Vero | New Guinea C | $4.10 \times 10^{*5}$ | $1.87 \times 10^{*6}$ |
| Dengue Virus Type 3 | Virus culture supernatant | LLC-MK2 | H87 | $1.70 \times 10^{*5}$ | $4.63 \times 10^{*7}$ |
| Dengue Virus Type 4 | Virus culture supernatant | Vero | H241 | $1.26 \times 10^{*6}$ | $2.87 \times 10^{*7}$ |
| West Nile Virus | Virus culture supernatant | LLC-MK2 | HNY1999 | $1.61 \times 10^{*7}$ | $2.10 \times 10^{*7}$ |

In order to find a range estimation of limit of detection (LoD), serial dilutions of the virus stocks described in Table 5 were prepared to provide for an initial estimation of LoD. For nucleic acid extraction, 225 µL of single donor serum aliquots were spiked individually with 25 µL of each serially diluted virus stock. The spiked serum mixes (250 µL in total) were extracted by NucliSENS® easyMag® (bioMérieux). Total Nucleic acid was eluted in 50 µL elution buffers and immediately stored on ice for further steps. Each sample was extracted in triplicate and tested with the CII-ArboPlex rRT-PCR assay on the CFX96™ touch Real-Time PCR Detection System (Bio-Rad) using the primers and probes described in Example 1 and materials and method described in Examples 2-4. Test results were only valid if samples were positive for RNase P (see Example 5). The lowest concentration at which all three replicates were tested positive was scored as the presumptive LoD. The serum LoD (genomic copy equivalent/ml) results are described in Table 6.

TABLE 6

Tentative Serum LoD Results

| Analyte | Virus Strain Tested | Stock Virus Titer (TCID50/mlL) | Serial 10-Fold Dilution Factor | TCID50/ mL Dilution Tested | Run 1 Ct | Run 2 Ct | Run 3 Ct | Average Ct | Call Rate | Virus copy number (GEQ/ml) |
|---|---|---|---|---|---|---|---|---|---|---|
| Zika Virus | PRVABC59 | 6.61 × 10*6 | 5 | 6.61 × 10*1 | 30.87 | 31.00 | 31.30 | 31.06 | 3/3 | 5.16E+03 |
| Dengue Virus Type 1 | Hawaii | 1.70 × 10*5 | 5 | 1.70 × 10*0 | 34.01 | 34.50 | 32.00 | 33.50 | 3/3 | 4.37E+02 |
| Dengue Virus Type 2 | New Guinea C | 4.1 × 10*5 | 5 | 4.1 × 10*0 | 31.54 | 32.00 | 31.90 | 31.81 | 3/3 | 1.87E+02 |
| Dengue Virus Type 3 | H87 | 1.70 × 10*5 | 5 | 1.70 × 10*0 | 34.01 | 35.00 | 34.60 | 34.54 | 3/3 | 4.63E+03 |
| Dengue Virus Type 4 | H241 | 1.26 × 10*6 | 5 | 1.26 × 10*1 | 34.40 | 34.80 | 34.40 | 34.53 | 3/3 | 2.87E+03 |
| Chikungunya virus | R80422 | 3.56 × 10*6 | 5 | 3.56 × 10*1 | 31.00 | 31.50 | 31.90 | 31.47 | 3/3 | 5.39E+03 |
| West Nile Virus | HNY1999 | 1.61 × 10*7 | 6 | 6.61 × 10*1 | 33.22 | 32.80 | 33.50 | 33.17 | 3/3 | 2.10E+02 |

Based on the LoD estimates determined in range-finding studies, virus stocks were diluted into 20 serum sample aliquots to give a final virus concentration at the presumptive LoD. Nucleic acids were extracted by NucliSENS® easyMag® (bioMérieux). All 20 extracted samples were tested with CII-ArboPlex rRT-PCR assay on the CFX96™ touch Real-Time PCR Detection System (Bio-Rad) as described in Examples 1-4. Results for all viruses in serum are shown in Table 7.

For nucleic acid extraction, 225 μL of single donor urine aliquots were spiked individually with 25 μL of each serially diluted virus stock. The spiked urine mixes (250 μL in total) were extracted by NucliSENS® easyMag® (bioMérieux). Total nucleic acid was eluted in 50 μL elution buffers and immediately stored on ice. Each sample was extracted in triplicate and tested with the CII-ArboPlex rRT-PCR assay on the CFX96™ touch Real-Time PCR Detection System (Bio-Rad) using the primers and probes described in

TABLE 7

Confirmation of LoD Using CII-ArboPlex rRT-PCR Assay for All Viruses in Serum

| No. of replicate | ZIKV Ct | DENV 1 Ct | DENV 2 Ct | DENV 3 Ct | DENV 4 Ct | CHIKV Ct | WNV Ct |
|---|---|---|---|---|---|---|---|
| Virus copy number (GEQ/ml) | 5.16E+03 | 4.37E+02 | 1.87E+02 | 4.63E+03 | 2.87E+04 | 5.39E+03 | 2.10E+02 |
| Replicate 1 | 31.86 | 32.87 | 31.05 | 33.68 | 31.81 | 31.65 | 33.81 |
| Replicate 2 | 31.68 | 34.41 | 31.28 | 30.93 | 32.01 | 31.68 | 33.68 |
| Replicate 3 | 31.79 | 33.52 | 31.16 | 31.95 | 31.68 | 31.59 | 34.00 |
| Replicate 4 | 32.47 | 32.67 | 32.52 | 30.45 | 30.67 | 31.36 | 32.81 |
| Replicate 5 | 32.69 | 33.49 | 32.51 | 30.28 | 30.77 | 31.39 | 32.62 |
| Replicate 6 | 32.70 | 33.42 | 32.58 | 31.44 | 30.54 | 31.01 | 32.50 |
| Replicate 7 | 30.42 | 31.93 | 32.29 | 30.18 | 31.85 | 31.26 | 34.19 |
| Replicate 8 | 30.38 | 32.81 | 32.14 | 30.42 | 32.04 | 31.64 | 34.22 |
| Replicate 9 | 30.48 | 32.41 | 32.49 | 31.42 | 31.56 | 31.63 | 33.60 |
| Replicate 10 | 32.02 | 32.35 | 32.88 | 30.5 | 30.78 | 31.87 | 33.90 |
| Replicate 11 | 32.70 | 32.89 | 32.27 | 31.85 | 30.72 | 31.72 | 33.92 |
| Replicate 12 | 32.65 | 33.23 | 33.09 | 31.48 | 30.90 | 31.26 | 33.93 |
| Replicate 13 | 31.58 | 32.90 | 32.40 | 30.7 | 31.23 | 31.34 | 33.39 |
| Replicate 14 | 31.24 | 32.73 | 33.54 | 30.53 | 30.99 | 31.12 | 33.17 |
| Replicate 15 | 31.23 | 32.82 | 33.26 | 30.73 | 31.16 | 31.44 | 33.31 |
| Replicate 16 | 32.64 | 33.60 | 35.34 | 31.36 | 31.67 | 31.76 | 33.38 |
| Replicate 17 | 32.24 | 31.66 | 32.14 | 31.09 | 31.34 | 31.51 | 33.95 |
| Replicate 18 | 32.48 | 31.31 | 31.69 | 30.05 | 31.35 | 32.08 | 33.31 |
| Replicate 19 | 31.48 | 31.96 | 31.55 | 30.49 | 30.46 | 31.94 | 33.30 |
| Replicate 20 | 31.49 | 34.45 | 32.34 | 30.67 | 30.45 | 31.19 | 33.26 |
| Average Ct | 31.81 | 32.87 | 32.43 | 31.01 | 31.20 | 31.52 | 33.51 |
| Call rate | 20/20 | 20/20 | 20/20 | 20/20 | 20/20 | 20/20 | 20/20 |
| Call rate % | 100% | 100% | 100% | 100% | 100% | 100% | 100% |

Example 7—Analytical Sensitivity Assessment of the Assay in Urine

Using the materials and methods set forth in Examples 1-5 and the virus stocks described in Table 5, the analytical sensitivity of the assay was tested in urine.

Example 1 and materials and method described in Examples 2-4. Test results were only valid if samples were positive for RNase P (see Example 5). The lowest concentration at which all three replicates tested positive was scored as the presumptive LoD (bold and highlighted for each virus). The urine LoD (GEQ/ml) results are described in Table 8.

TABLE 8

Tentative Urine LoD Results

| Analyte | Virus Strain Tested | Stock Virus Titer (TCID50/mlL) | Serial 10-Fold Dilution Factor | TCID50/mL Dilution Tested | Run 1 Ct | Run 2 Ct | Run 3 Ct | Average Ct | Call Rate | Virus copy number (GEQ/ml) |
|---|---|---|---|---|---|---|---|---|---|---|
| Zika Virus | PRVABC59 | $6.61 \times 10^{*}6$ | 5 | $6.61 \times 10^{*}1$ | 33.91 | 32.50 | 31.76 | 32.72 | 3/3 | 5.16E+03 |
| Dengue Virus Type 1 | Hawaii | $1.70 \times 10^{*}5$ | 4 | $1.70 \times 10^{*}1$ | 31.66 | 32.69 | 31.01 | 31.79 | 3/3 | 4.37E+03 |
| Dengue Virus Type 2 | New Guinea C | $4.1 \times 10^{*}5$ | 5 | $4.1 \times 10^{*}0$ | 33.21 | 32.50 | 33.47 | 33.06 | 3/3 | 1.87E+02 |
| Dengue Virus Type 3 | H87 | $1.70 \times 10^{*}5$ | 5 | $1.70 \times 10^{*}0$ | 32.05 | 32.30 | 31.85 | 32.07 | 3/3 | 4.63E+03 |
| Dengue Virus Type 4 | H241 | $1.26 \times 10^{*}6$ | 5 | $1.26 \times 10^{*}1$ | 34.18 | 33.83 | 32.90 | 33.64 | 3/3 | 2.87E+03 |
| Chikungunya virus | R80422 | $3.56 \times 10^{*}6$ | 6 | $3.56 \times 10^{*}0$ | 33.61 | 32.50 | 32.90 | 33.00 | 3/3 | 5.39E+02 |
| West Nile Virus | HNY1999 | $1.61 \times 10^{*}7$ | 5 | $6.61 \times 10^{*}2$ | 32.74 | 32.50 | 32.88 | 32.71 | 3/3 | 2.10E+03 |

Based on the presumptive LoD, diluted virus stocks were spiked into 20 urine sample aliquots at the tentative LoD. Nucleic acids were extracted by NucliSENS® easyMag® (bioMérieux). All 20 extracted samples were tested with CII-ArboPlex rRT-PCR assay on the CFX96™ touch Real-Time PCR Detection System (Bio-Rad) as described in Examples 1-4. Results for all viruses in serum are shown in Table 9.

TABLE 9

Confirmation of LoD Using CII-ArboPlex rRT-PCR Assay for All Viruses in Urine

| No. of replicate | ZIKV Ct | DENV 1 Ct | DENV 2 Ct | DENV 3 Ct | DENV 4 Ct | CHIKV Ct | WNV Ct |
|---|---|---|---|---|---|---|---|
| Virus copy number (GEQ/ml) (GEQ/ml) | 5.16E+03 | 4.37E+03 | 1.87E+02 | 4.63E+03 | 2.87E+03 | 5.39E+02 | 2.10E+03 |
| Replicate 1 | 32.76 | 32.71 | 31.57 | 32.07 | 32.77 | 31.89 | 34.20 |
| Replicate 2 | 32.89 | 31.88 | 31.50 | 31.69 | 32.51 | 32.05 | 34.71 |
| Replicate 3 | 32.84 | 31.56 | 31.57 | 33.23 | 32.09 | 31.95 | 34.32 |
| Replicate 4 | 33.02 | 31.85 | 30.83 | 32.44 | 33.69 | 32.19 | 33.75 |
| Replicate 5 | 32.85 | 33.34 | 30.84 | 32.33 | 32.22 | 32.55 | 33.32 |
| Replicate 6 | 32.76 | 32.69 | 30.92 | 32.89 | 32.01 | 32.34 | 33.40 |
| Replicate 7 | 33.13 | 31.43 | 32.78 | 32.37 | 32.61 | 32.34 | 33.44 |
| Replicate 8 | 33.71 | 32.35 | 33.05 | 33.93 | 32.97 | 32.61 | 33.24 |
| Replicate 9 | 32.74 | 31.72 | 32.99 | 32.08 | 32.64 | 33.07 | 33.22 |
| Replicate 10 | 32.82 | 31.53 | 31.68 | 32.17 | 31.64 | 32.33 | 33.32 |
| Replicate 11 | 33.02 | 32.12 | 31.83 | 32.49 | 31.66 | 32.55 | 33.75 |
| Replicate 12 | 33.04 | 31.76 | 31.80 | 32.00 | 31.51 | 32.51 | 33.54 |
| Replicate 13 | 33.14 | 32.87 | 31.76 | 33.06 | 33.19 | 32.40 | 34.51 |
| Replicate 14 | 32.70 | 32.03 | 31.93 | 32.54 | 31.86 | 32.56 | 34.57 |
| Replicate 15 | 32.68 | 32.16 | 31.86 | 33.02 | 32.36 | 32.31 | 34.04 |
| Replicate 16 | 33.04 | 31.56 | 32.55 | 32.31 | 33.67 | 31.60 | 34.30 |
| Replicate 17 | 33.37 | 31.42 | 32.68 | 32.41 | 32.66 | 31.77 | 34.11 |
| Replicate 18 | 32.92 | 31.44 | 32.73 | 34.17 | 32.77 | 31.76 | 34.61 |
| Replicate 19 | 31.98 | 31.26 | 32.90 | 32.59 | 31.57 | 31.87 | 33.53 |
| Replicate 20 | 31.78 | 31.19 | 33.06 | 33.12 | 31.88 | 31.83 | 33.21 |
| Average Ct | 32.86 | 31.94 | 32.04 | 32.65 | 32.41 | 32.22 | 33.85 |
| Call rate | 20/20 | 20/20 | 20/20 | 20/20 | 20/20 | 20/20 | 20/20 |
| Call rate % | 100% | 100% | 100% | 100% | 100% | 100% | 100% |

Example 8—Analytical Specificity Testing

Reactivity of the CII-ArboPlex rRT-PCR was evaluated by wet testing of additional isolates of Zika virus representing the African isolates (MR776 and ArD158095) using materials and methods of Examples 1-5.

TABLE 10

Details of Additional ZIKV Evaluated by CII-ArboPlex rRT-PCR

| Zika Virus Isolate | Source/ Sample Type* | Concentration (GEQ/ml) | CDC Trioplex Assay (Ct) | CII-ArboViroPlex |
|---|---|---|---|---|
| ZIKV MR776 | Virus culture | $1.70 \times 10^{*6}$ | 16.52 | 15.85 |
| ZIKV ArD158095 | In vitro transcribed RNA | $1.40 \times 10^{*6}$ | 15.98 | 15.11 |

Reactivity of primers and probes described in Example 1 were also tested in silico with other representative isolates of ZIKV, DENV, CHIKV and WNV using the materials and methods of Examples 2-5.

The following strains of West Nile virus were used (followed by GenBank Accession number): ARC10-06 (JF957161); ARC13-06 (JF957162); ARC-17-06 (JF957163); ARC23-06 (JF957164); ARC27-06 (JF957165); ARC33-06 (JF957166); BSL106-06 (JF957167); AR140-07 (JF957168); CO4-07 (JF957169); CO5-07 (JF957170); ID21bird-07 (JF957171); ID28bird-07 (JF957172); BSL173-08 (JF957173); BSL176-08 (JF957174); BSL2-09 (JF957175); BSL5-09 (JF957176); BSL6-09 (JF957177); BSL11-09 (JF957178); BSL18-09 (JF957179); BSL20-09 (JF957180); BSL22-09 (JF957181); BSL24-09 (JF957182); BSL27-09 (JF957183); CO7-09 (JF957184); BSL2-10 (JF957185); BSL3-10 (JF957186); NY10-03 (JQ700437); BSL4-11 (JQ700438); BSL6-11 (JQ700439); BSL23-11 (JQ700440); BSL24-11 (JQ700441); and BSL26-11 (JQ700442).

The following strains of Zika virus were used (followed by GenBank Accession number): PRVABC59 (KU501215); MR 766 (AY632535); FLR (KU820897); C1/C2 (KX087102); IbH_30656 (HQ234500); IbH-30656 (KU963574); SEN-DAK (KU955592); 17271 (KU758877); Paraiba_01 (KX280026); 103451 (KX262887); ZKC (KX253996); COL/UF-1 (KX247646); MEX_I_7 (KX247632); PAN/BEI-259634_V4 (KX198135); Brazil/PE243 (KX197192); CN/SZ02 (KX185891); ZIKVNL00013 (KU937936); PAN/CDC-259359 (KX156776); /PAN/CDC-259249 (KX156775); PAN/CDC-259359 (KX156774); Bahia01 (KX101066); Zhejiang04 (KX117076); Haiti/1/2016 (KX051563); Haiti/1225/2014 (KU509998); SZ-WIV01 (KU963796); Brazil/2016/INMI1 (KU991811); Bahia07 (KU940228); Bahia09 (KU940224); Z16006 (KU955589); FB-GWUH-2016 (KU870645); Rio-S1 (KU926310); Rio-U1 (KU926309); MEX/InDRE/Sm/2016 (KU922960); MEX/InDRE/Lm/2016 (KU922923); SZ01 (KU866423); GZ01 (KU820898); GD01 (KU740184); DR/2016/PD2 (KU853013) DR/2016/PD1 (KU853012); ZJ03 (KU820899); BeH823339 (KU729217); BeH828305 (KU729218); GDZ16001 (KU761564); THA/2014 (KU681081); VE_Ganxian (KU744693); Brazil-ZKV2015 (KU497555); SSABR1, (KU707826); Natal RGN (KU527068); MRS_OPY (KU647676); 8375 (KU501217); 103344 (KU501216); BeH815744 (KU365780); BeH819966 (KU365779); BeH819015 (KU365778); BeH818995 (KU365777); Z1106033 (KU312312); ZikaSPH2015, (KU321639); H/PF/2013 (KJ776791); GZ02/2016 (KX056898); Z16019 (KU955590); KHM/2010 (KU955593); PLCal_ZV (KF993678); FSS13025 (JN860885); CPC-0740 (KU681082); Tahiti (KJ461621); ArD128000 (KF383117); P6-740 (HQ234499); SEN/DAK-AR-41524 (KX198134); 41671-DAK (KU955595); 41525-DAK (KU955591); ArD142623 (KF383120); ArD7117 (KF383116); ArD_41519 (HQ234501); ArD158095 (KF383121); ArD158084 (KF383119); ArD157995 (KF383118); ARB7701 (KF268950); ARB15076 (KF268949); ARB13565 (KF268948); and ArB1362 (KF383115);

The following strains of DENV virus were used (followed by GenBank Accession number): Brazil 2010 (JX669466); Thailand 2013 (KF887994); Mexico 2012 (KJ189368); Brazil 2010 (JX669477); Peru 2011 (KC294210); Indonesia 2010 (KC762679); Saudi Arabia 2014 (KJ830750); Singapore 2012 (KM279577); Thailand 2010 (HG316483); Brazil 2009 (JF808120); Indonesia 2010 (KC762693); China 2013 (KJ622195); Singapore 2005 (GQ398256); Venezuela 2007 (HQ332174); Cambodia 2008 (JN638570); Brazil 2010 (JN983813); and Pakistan 2009 (KF041260).

The following strains of CHIKV virus were used (followed by GenBank Accession number): Philippines 2013 (AB860301); Singapore 2008 (FJ445463); Sri Lanka 2008 (FJ513654); Malaysia 2008 (FJ807899); China 2008 (GU199351); India 2008 (JN558835); China 2012 (KC488650); Thailand 2013 (KJ579186); Indonesia 2013 (KM673291); Rep of Congo 2011 (KP003813); Mexico 2014 (KP851709); Trinidad & Tobago 2014 (KR046231); Brazil 2014 (KR264951); El Salvador 2014 (KR559471); French Polynesia 2015 (KR559473); Puerto Rico 2014 (KR559474); Honduras 2014 (KR559488); Jamaica 2014 (KR559489); Guyana 2014 (KR559496); and India 2013 (KT336782).

In almost every test, the primers and probes from each virus were 100% reactive with the representative isolate of the virus, and in the very few cases that was not 100% the reactivity was at least 95%. The reactivity of the primers and probes from each virus were less than about 24% to less than about 70% reactive with the representative isolates of the other viruses.

Example 9—Cross-Reactivity of the Probes and Primers

Cross-reactivity of the CII-ArboPlex rRT-PCR was evaluated by testing additional Flaviviruses or purified nucleic acid from other febrile illness due to infection with other viruses and pathogenic bacteria.

To evaluate the analytical specificity of the CII-ArboPlex rRT-PCR assay, samples containing nucleic acids representing a wide range of human pathogens not targeted in the CII-ArboPlex rRT-PCR assay using the materials and methods from Examples 1-5, in particular with the primer and probes in Table 1. Nucleic acids were extracted from cell culture supernatant or clinical specimens banked at the Center for Infection and Immunity, or provided by the NIH-Integrated Research Facility (Fort Detrick, Md.). Samples tested with CII-ArboPlex rRT-PCR assay on the CFX96™ touch Real-Time PCR Detection System (Bio-Rad) showed no evidence of cross-reactivity. Test results were only considered valid if samples were positive for the host transcript control RNase P. Results are shown in Table 11.

TABLE 11

Results of Specificity of CII-ArboPlex rRT-PCR assay

| Virus/Bacteria/Parasite | Strain | Source/Sample type | Concentration | Average Ct |
|---|---|---|---|---|
| Yellow fever virus | 17D-204 | Extracted nucleic acid | $2.1 \times 10^5$ PFU/ml | ND |
| Japanese encephalitis virus | Nakayama | Extracted nucleic acid | $\sim 1.5 \times 10^7$ GEQ/ml | ND |
| Saint Louis encephalitis virus | Unknown | Extracted nucleic acid | $\sim 1.0 \times 10^5$ GEQ/ml | ND |
| Hepatitis C virus | Clinical isolate | Extracted nucleic acid | $1.6 \times 10^6$ GEQ/ml | ND |
| Enterovirus D68 | F02-3607 Corn | Virus culture | $1.1 \times 10^7$ GEQ/ml | ND |
| Influenza A virus | H3N2-Panama | Virus culture | $1 \times 10^9$ TCID$_{50}$/ml | ND |
| Human Adenovirus 6 | HADV-6 | Virus culture | $1.64 \times 10^5$ TCID$_{50}$/ml | ND |
| Human herpes virus 1 | KOS | Virus culture | $1 \times 10^{11}$ TCID$_{50}$/ml | ND |
| Ebola virus | Makona | Extracted nucleic acid | $1.3 \times 10^5$ PFU/ml | ND |
| Parvovirus B19 | Clinical isolate | Extracted nucleic acid | $\sim 5.0 \times 10^6$ GEQ/ml | ND |
| Lassa virus | Josiah | Extracted nucleic acid | $2.1 \times 10^5$ PFU/ml | ND |
| Plasmodium falciparum | Clinical isolate | Extracted nucleic acid | $1.5 \times 10^7$ GEQ/ml | ND |
| Salmonella Typhi | Clinical isolate | Extracted nucleic acid | $2.9 \times 10^5$ GEQ/ml | ND |
| E. Coli | DH5a | Bacterial Culture | NA | ND |

ND=No Detection.

In silico analysis was performed for other agents not available for laboratory testing. Sequences of the primers and probes in Example 1 and Table 1 were evaluated for evidence of cross-reactivity against the species listed in Table 14. Analyses using the BLAST algorithm were performed using all possible combinations of primer/probes. Any correlations based on computational alignment were reviewed for potential formation of a PCR product through binding of the primers in close proximity and with the right orientation to each other flanking a probe on target nucleic acid.

For virtually every species listed in Table 12, the probes and primers set forth in Example 1 had less than 20% cross-reactivity.

TABLE 12

Other species used for testing assay

| Other Flaviviruses | AccNo/TaxID | Description |
|---|---|---|
| St. Louis encephalitis virus | NC_007580.2 | St. Louis encephalitis virus, complete genome |
| Japanese encephalitis virus | NC_001437.1 | Japanese encephalitis virus, genome |
| Spondweni virus | NC_029055.1 | Spondweni virus, complete genome |
| Hepatitis C virus | (taxid: 11102) | Hepatitis C virus group |
| yellow fever virus | NC_002031.1 | Yellow fever virus, complete genome |
| yellow fever virus vaccine strain | FJ654700.1 | Yellow fever virus 17D/Tiantan, complete genome |
| Eastern Equine Encephalitis Virus (EEE) | NC_003899.1 | Eastern equine encephalitis virus, complete genome |
| Western Equine Encephalitis Virus (WEE) | NC_003908.1 | Western equine encephalomyelitis virus, complete genome |
| Ross River virus | NC_001544.1 | Ross River virus, complete genome |
| Barmah Forest virus | NC_001786.1 | Barmah Forest virus, complete genome |
| O'nyong-nyong virus | NC_001512.1 | O'nyong-nyong virus, complete genome |
| (Sindbis virus, Tonate virus and Una virus) | NC_001547.1 | Sindbis virus, complete genome |
| Measles virus | NC_001498.1 | Measles virus, complete genome |
| Rubella virus | NC_001545.2 | Rubella virus, complete genome |
| Enterovirus all serotypes | NC_001430.1 | Human enterovirus D, complete genome |
| | NC_001472.1 | Human enterovirus B, complete genome |
| | NC_001490.1 | Human rhinovirus 14, complete genome |
| | NC_001612.1 | Human enterovirus A, complete genome |
| | NC_001617.1 | Human rhinovirus 89, complete genome |
| | NC_001859.1 | Bovine enterovirus, complete genome |
| | NC_002058.3 | Poliovirus, complete genome |
| | NC_003985.1 | Porcine teschovirus 1, complete genome |
| | NC_003987.1 | Porcine sapelovirus 1, complete genome |
| | NC_003988.1 | Simian enterovirus A, complete genome |
| | NC_004441.1 | Porcine enterovirus 9 strain UKG/410/73 polyprotein gene, |
| | NC_006553.1 | Avian sapelovirus, complete genome |
| | NC_008714.1 | Possum enterovirus W1, complete genome |
| | NC_009996.1 | Human rhinovirus C, complete genome |
| | NC_010415.1 | Enterovirus J strain 1631, complete genome |
| | NC_013695.1 | Enterovirus J strain N203, complete genome |
| | NC_021220.1 | Enterovirus F strain BEV-261 polyprotein gene, complete |

TABLE 12-continued

Other species used for testing assay

| Other Flaviviruses | AccNo/TaxID | Description |
|---|---|---|
| | NC_024073.1 | Enterovirus sp. isolate CPML_8109/08, complete genome |
| | NC_029854.1 | Yak enterovirus strain SWUN-AB001, complete genome |
| | NC_029905.1 | Enterovirus SEV-gx, complete genome |
| | NC_030454.1 | Human enterovirus strain V13-0285, partial genome |
| Adenovirus—all serotypes | AC_000001.1 | Ovine adenovirus A, complete genome |
| | AC_000002.1 | Bovine adenovirus B, complete genome |
| | AC_000003.1 | Canine adenovirus 1, complete genome |
| | AC_000004.1 | Duck adenovirus A, complete genome |
| | AC_000005.1 | Human mastadenovirus A |
| | AC_000006.1 | Human adenovirus D, complete genome |
| | AC_000007.1 | Human adenovirus 2, complete genome |
| | AC_000008.1 | Human adenovirus 5, complete genome |
| | AC_000009.1 | Porcine adenovirus C, complete genome |
| | AC_000010.1 | Simian adenovirus 21, complete genome |
| | AC_000011.1 | Simian adenovirus 25, complete genome |
| | AC_000012.1 | Murine adenovirus A, complete genome |
| | AC_000013.1 | Fowl adenovirus D, complete genome |
| | AC_000014.1 | Fowl adenovirus A, complete genome |
| | AC_000016.1 | Turkey adenovirus A, complete genome |
| | AC_000017.1 | Human adenovirus type 1, complete genome |
| | AC_000018.1 | Human adenovirus type 7, complete genome |
| | AC_000019.1 | Human adenovirus type 35, complete genome |
| | AC_000020.1 | Canine adenovirus type 2, complete genome |
| | AC_000189.1 | Porcine adenovirus 3, complete genome |
| | AC_000190.1 | Tree shrew adenovirus 1, complete genome |
| | AC_000191.1 | Bovine adenovirus A, complete genome |
| | NC_000899.1 | Fowl adenovirus D, complete genome |
| | NC_000942.1 | Murine adenovirus A, complete genome |
| | NC_001405.1 | Human adenovirus C, complete genome |
| | NC_001454.1 | Human adenovirus F, complete genome |
| | NC_001460.1 | Human adenovirus A, complete genome |
| | NC_001720.1 | Fowl adenovirus A, complete genome |
| | NC_001734.1 | Canine adenovirus, complete genome |
| | NC_001813.1 | Duck adenovirus A, complete genome |
| | NC_001876.1 | Bovine adenovirus 3 complete genome |
| | NC_001958.1 | Hemorrhagic enteritis virus, complete genome |
| | NC_002501.1 | Frog adenovirus 1, complete genome |
| | NC_002513.1 | Bovine adenovirus type 2, complete genome |
| | NC_002685.2 | Bovine adenovirus D, complete genome |
| | NC_002702.1 | Porcine adenovirus 5, complete genome |
| | NC_003266.2 | Human adenovirus E, complete genome |
| | NC_003375.1 | Garlic virus A, complete genome |
| | NC_004037.2 | Ovine adenovirus 7, complete genome |
| | NC_005889.1 | Bovine adeno-associated virus, complete genome |
| | NC_006144.1 | Simian adenovirus 3, complete genome |
| | NC_006150.1 | Macacine herpesvirus 3, complete genome |
| | NC_006879.1 | Simian adenovirus 1, complete genome |
| | NC_009989.1 | Snake adenovirus, complete genome |
| | NC_010956.1 | Human adenovirus D, complete genome |
| | NC_011103.1 | Rhizobium phage 16-3, complete genome |
| | NC_011202.1 | Human adenovirus B2, complete genome |
| | NC_011203.1 | Human adenovirus B1, complete genome |
| | NC_012584.1 | Murine adenovirus 3, complete genome |
| | NC_012783.2 | Cercopithecine herpesvirus 5 strain 2715, complete genome |
| | NC_012959.1 | Human adenovirus 54, complete genome |
| | NC_014564.2 | Turkey adenovirus 1, complete genome |
| | NC_014899.1 | Murine adenovirus 2, complete genome |
| | NC_014969.1 | Fowl adenovirus E, complete genome |
| | NC_015123.1 | Japanese eel endothelial cells-infecting virus, complete genome |
| | NC_015225.1 | Simian adenovirus 49, complete genome |
| | NC_015323.1 | Fowl adenovirus C, complete genome |
| | NC_015455.1 | Raptor adenovirus A, complete genome |
| | NC_015932.1 | Bat adenovirus 2, complete genome |
| | NC_016437.1 | South polar skua adenovirus-1, complete genome |
| | NC_016895.1 | Bat adenovirus TJM, complete genome |
| | NC_017825.1 | Chimpanzee adenovirus Y25, complete genome |

TABLE 12-continued

Other species used for testing assay

| Other Flaviviruses | AccNo/TaxID | Description |
|---|---|---|
| | NC_017979.1 | Goose adenovirus 4, complete genome |
| | NC_020074.1 | Bovine adenovirus 6 strain 671130, complete genome |
| | NC_020485.1 | Simian adenovirus 20 strain ATCC VR-541, complete genome |
| | NC_020487.1 | Titi monkey adenovirus ECC-2011, complete genome |
| | NC_021168.1 | Simian adenovirus C isolate BaAdV-2, complete genome |
| | NC_021221.1 | Fowl adenovirus 5 strain 340, complete genome |
| | NC_021858.1 | Pandoravirus dulcis, complete genome |
| | NC_022266.1 | Simian adenovirus 18, complete genome |
| | NC_022612.1 | Turkey adenovirus 4 isolate TNI1, complete genome |
| | NC_022613.1 | Turkey adenovirus 5 isolate 1277BT, complete genome |
| | NC_022915.1 | Ralstonia phage RSK1 DNA, complete genome |
| | NC_024150.1 | California sea lion adenovirus 1 strain Zc11-030, complete genome |
| | NC_024474.1 | Pigeon adenovirus 1 complete genome, strain IDA4 |
| | NC_024486.1 | Duck adenovirus 2 strain GR, complete genome |
| | NC_024684.1 | Lizard adenovirus 2 isolate 23-06, complete genome |
| | NC_025678.1 | Simian adenovirus DM-2014 isolate 23336, complete genome |
| | NC_025962.1 | Psittacine adenovirus 3 isolate HKU/Parrot19, complete genome |
| | NC_027705.1 | Equine adenovirus 2 isolate EAdV2.385/75.9, complete genome |
| | NC_027708.1 | Skunk adenovirus PB1, complete genome |
| | NC_028103.1 | Simian adenovirus 13 strain P-9, complete genome |
| | NC_028105.1 | Simian adenovirus 16 strain C-8, complete genome |
| | NC_028107.1 | Simian adenovirus 19 strain AA153, complete genome |
| | NC_028113.1 | Simian adenovirus 8 strain P-5, complete genome |
| | NC_030116.1 | Unidentified adenovirus isolate CSPAdV_2, complete genome |
| | NC_030230.1 | Tokyovirus A1 DNA, nearly complete genome |
| | NC_030792.1 | Equine adenovirus 1 strain M1, complete genome |
| | NC_031503.1 | Pigeon adenovirus 2 isolate YPDS-Y-V1.A19.11-2013, complete genome |
| Hepatitis B virus | NC_001344.1 | Duck hepatitis B virus, complete genome |
| | NC_001484.1 | Ground squirrel hepatitis virus, complete genome |
| | NC_001486.1 | Heron hepatitis B virus, complete genome |
| | NC_003977.2 | Hepatitis B virus (strain ayw) genome |
| | NC_005888.1 | Ross's goose hepatitis B virus, complete genome |
| | NC_005890.1 | Sheldgoose hepatitis B virus, complete genome |
| | NC_005950.1 | Snow goose hepatitis B virus, complete genome |
| | NC_016561.1 | Parrot hepatitis B virus, complete genome |
| | NC_024443.1 | Roundleaf bat hepatitis B virus isolate complete genome |
| | NC_024444.1 | Horseshoe bat hepatitis B virus isolate complete genome |
| | NC_024445.1 | Tent-making bat hepatitis B virus isolate complete genome |
| | NC_028129.1 | Woolly monkey hepatitis B virus clone WMHBV-2, complete genome |
| HIV | NC_001802.1 | Human immunodeficiency virus 1, complete genome |
| Varicella Zoster virus | NC_001348.1 | Human herpesvirus 3, complete genome |
| Cytomegalovirus (CMV) | NC_006273.2 | Human herpesvirus 5 strain Merlin, complete genome |
| Epstein Barr Virus (EBV) | NC_007605.1 | Human herpesvirus 4 complete wild type genome |
| *Rickettsia* sp. | AB021128.1 | *Rickettsia* sp. (Kytorhinus sharpianus symbiont) gene for 16S rRNA, partial sequence |
| *Borrelia burgdorferi* | (taxid: 64895) | *Borrelia burgdorferi* group |
| Group A *Streptococcus* | KX998201.1 | *Streptococcus* sp. strain J-F-03 16S ribosomal RNA gene, partial sequence |

TABLE 12-continued

Other species used for testing assay

| Other Flaviviruses | AccNo/TaxID | Description |
|---|---|---|
| Leptospirosis | NC_004343.2 | *Leptospira interrogans* serovar Lai str. 56601 chromosome II, complete sequence |
| Plasmodium sp. | LT594489.1 | Plasmodium sp. genome assembly, chromosome: 1 |
| Plasmodium vivax | NC_009906.1 | Plasmodium vivax SaI-1 chromosome 1, whole genome shotgun sequence |
| Trypanosoma cruzi (Chagas) | (taxid: 5693) | Trypanosoma cruzi |
| Schistosomiasis | (taxid: 6181) | Schistosoma |
| Hepatitis A virus vaccine—BIOVAC-A brand | (taxid: 12092) | Hepatovirus A |
| *Salmonella typhi* vaccine (Typhoid—Ty21a vaccine) | CP002099.1 | *Salmonella* enterica subsp. enterica serovar Typhi str. Ty21a, complete genome |

Example 10—Clinical Evaluation of Zika Virus

Contrived samples for clinical evaluation study were prepared by spiking 1× LoD and 3× LoD virus in 13 negative control serum samples and 13 negative control urine samples collected from individual patients with febrile illness but no indication of viral infection. Positive specimens were obtained through NYCDOHMH, NYSDOH and Boca Biolistics, FL, USA. The comparator assays used to identify ZIKV positive samples were the LightMix Zika rRT-PCR test (Roche) or Aptima Zika Virus assay (HOLOGIC, PRD-04037-D) at Boca Biolistics or NYS-approved LDT assays at NYCDOHMH and NYSDOH, which is a modification of a CDC-published assay Lanciotti, et al. Results for clinical sample evaluation with CII-ArboViroPlex rRT-PCR assay are shown in Tables 13-16. Results for paired urine and serum samples are shown in Table 13; unpaired serum samples are shown in Table 14; unpaired urine samples in Table 15; and for contrived urine and serum samples in Table 16.

In all cases the CII-ArboPlex rRT-PCR assay using Primers SEQ ID NOs: 1 and 2 and Probe SEQ ID NO: 3 was positive for the ZIKV positive samples.

Summary of Clinical samples evaluation for Zika virus with CII-ArboPlex rRT-PCR assay using Primers SEQ ID NOs: 1 and 2 and Probe SEQ ID NO: 3.

Total n=115 (serum, n=65; urine, n=50)

Total Serum Samples n=65 positive samples

Clinical n=39 (paired serum/urine, n=7; unpaired, n=32)

Contrived n=26 (n=13 at 1× LoD, this being 5.16E+03 GEQ/ml;

and n=13 at 3× LoD, this being 1.54 E+04 GEQ/ml)

Total Urine Samples n=50 positive Samples

Clinical n=24 (paired serum/urine, n=7; unpaired, n=17)

Contrived n=26 (n=13 at 1× LoD, this being 5.16E+03 GEQ/ml and n=13 at 3× LoD, this being 1.54 E+04 GEQ/ml)

TABLE 13

Results of Performance of Assay for ZIKV in Paired Urine and Serum Samples

| | Sample ID | Sample Type | Tests performed at | Reference Assay used | Reference Assay (Ct for LightMix or S/CO for Aptima) | CII ArboViroPlex rRT PCR Assay (Ct) | Known or Potential Positive Agent |
|---|---|---|---|---|---|---|---|
| 1 | 1043-TDS-0428 | SERUM | Boca Biolistics | LightMix Zika rRT-PCR test | 32.49 | 37.14 | ZIKA |
| 2 | 1043-TDS-0428 | URINE | Boca Biolistics | Aptima Zika Virus Assay | 34.23 | 26.02 | ZIKA |
| 3 | 1043-TDS-0052 | SERUM | Boca Biolistics | LightMix Zika rRT-PCR test | 35.12 | 26.26 | ZIKA |
| 4 | 1043-TDS-0052 | URINE | Boca Biolistics | Aptima Zika Virus Assay | 33.84 | 30.03 | ZIKA |
| 5 | 1043-TDS-0332 | SERUM | Boca Biolistics | LightMix Zika rRT-PCR test | 32.64 | 26.5 | ZIKA |
| 6 | 1043-TDS-0332 | URINE | Boca Biolistics | Aptima Zika Virus Assay | 35.58 | 37.19 | ZIKA |
| 7 | 1043-TDS-0257 | SERUM | Boca Biolistics | LightMix Zika rRT-PCR test | 32.8 | 27.55 | ZIKA |
| 8 | 1043-TDS-0257 | URINE | Boca Biolistics | Aptima Zika Virus Assay | 33.26 | 27.04 | ZIKA |
| 9 | 1043-TDS-0211 | SERUM | Boca Biolistics | LightMix Zika rRT-PCR test | 32.32 | 28.92 | ZIKA |
| 10 | 1043-TDS-0211 | URINE | Boca Biolistics | Aptima Zika Virus Assay | 19.56 | 34.51 | ZIKA |
| 11 | 200556739 | SERUM | NYSDOH | NYS-approved LDT (Lanciotti et al) | 32.01 | 27.85 | ZIKA |

TABLE 13-continued

Results of Performance of Assay for ZIKV in Paired Urine and Serum Samples

| Sample ID | Sample Type | Tests performed at | Reference Assay used | Reference Assay (Ct for LightMix or S/CO for Aptima) | CII ArboViroPlex rRT PCR Assay (Ct) | Known or Potential Positive Agent |
|---|---|---|---|---|---|---|
| 12 200556738 | URINE | NYSDOH | NYS-approved LDT (Lanciotti et al) | 36.36 | 29.44 | ZIKA |
| 13 200555055 | SERUM | NYSDOH | NYS-approved LDT (Lanciotti et al) | 33.02 | 28.36 | ZIKA |
| 14 200555056 | URINE | NYSDOH | NYS-approved LDT (Lanciotti et al) | 35.53 | 26.69 | ZIKA |

TABLE 14

Results of Performance of Assay for ZIKV in Unpaired Serum Samples

| Sample ID | Sample Type | Tests performed at | Reference Assay used | Reference Assay (Ct for LightMix or S/CO for Aptima) | CII ArboViroPlex rRT PCR Assay (Ct) | Known or Potential Positive Agent |
|---|---|---|---|---|---|---|
| 1 1043-TDS-0127 | SERUM | Boca Biolistics | LightMix Zika rRT-PCR test | 32.95 | 20.28 | ZIKA |
| 2 1043-TDS-0474 | SERUM | Boca Biolistics | LightMix Zika rRT-PCR test | 34.31 | 25.96 | ZIKA |
| 3 1043-TDS-0216 | SERUM | Boca Biolistics | LightMix Zika rRT-PCR test | 33.81 | 33.49 | ZIKA |
| 4 1043-TDS-0440 | SERUM | Boca Biolistics | LightMix Zika rRT-PCR test | 32.08 | 26.35 | ZIKA |
| 5 1043-TDS-0085 | SERUM | Boca Biolistics | LightMix Zika rRT-PCR test | 33.04 | 31.98 | ZIKA |
| 6 1043-TDS-0269 | SERUM | Boca Biolistics | LightMix Zika rRT-PCR test | 33.82 | 26.08 | ZIKA |
| 7 1043-TDS-0433 | SERUM | Boca Biolistics | LightMix Zika rRT-PCR test | 33.55 | 27.77 | ZIKA |
| 8 1043-TDS-0183 | SERUM | Boca Biolistics | LightMix Zika rRT-PCR test | 33.64 | 26.19 | ZIKA |
| 9 1043-TDS-0354 | SERUM | Boca Biolistics | LightMix Zika rRT-PCR test | 31.01 | 26.85 | ZIKA |
| 10 1043-TDS-0499 | SERUM | Boca Biolistics | LightMix Zika rRT-PCR test | 33.87 | 30.26 | ZIKA |
| 11 1043-TDS-0071 | SERUM | Boca Biolistics | LightMix Zika rRT-PCR test | 34.57 | 29.2 | ZIKA |
| 12 1043-TDS-0353 | SERUM | Boca Biolistics | LightMix Zika rRT-PCR test | 30.24 | 28.32 | ZIKA |
| 13 1043-TDS-0297 | SERUM | Boca Biolistics | LightMix Zika rRT-PCR test | 36.94 | 29.65 | ZIKA |
| 14 200495232 | SERUM | NYSDOH | NYS-approved LDT (Lanciotti et al) | 30.99 | 23.92 | Zika |
| 15 200497235 | SERUM | NYSDOH | NYS-approved LDT (Lanciotti et al) | 35.96 | 26.64 | Zika |
| 16 200501025 | SERUM | NYSDOH | NYS-approved LDT (Lanciotti et al) | 27.85 | 28.87 | Zika |
| 17 200504978 | SERUM | NYSDOH | NYS-approved LDT (Lanciotti et al) | 37.25 | 28.62 | Zika |
| 18 200506171 | SERUM | NYSDOH | NYS-approved LDT (Lanciotti et al) | 37.89 | 34.2 | Zika |
| 19 IDR1600035343-01 | SERUM | NYSDOH | NYS-approved LDT (Lanciotti et al) | 33.01 | 32.26 | ZIKA |
| 20 IDR1600032120-01 | SERUM | NYSDOH | NYS-approved LDT (Lanciotti et al) | 39.09 | 36.63 | ZIKA |
| 21 IDR1600034229-01 | SERUM | NYSDOH | NYS-approved LDT (Lanciotti et al) | 33.84 | 27.1 | ZIKA |

TABLE 14-continued

Results of Performance of Assay for ZIKV in Unpaired Serum Samples

|    | Sample ID | Sample Type | Tests performed at | Reference Assay used | Reference Assay (Ct for LightMix or S/CO for Aptima) | CII ArboViroPlex rRT PCR Assay (Ct) | Known or Potential Positive Agent |
|----|-----------|-------------|--------------------|----------------------|------------------------------------------------------|-------------------------------------|-----------------------------------|
| 22 | IDR1600035381-01 | SERUM | NYSDOH | NYS-approved LDT (Lanciotti et al) | 38.9 | 31.82 | ZIKA |
| 23 | IDR1600036135-01 | SERUM | NYSDOH | NYS-approved LDT (Lanciotti et al) | 36.21 | 29 | ZIKA |
| 24 | 200536683 | SERUM | NYSDOH | NYS-approved LDT (Lanciotti et al) | 25.69 | 23.27 | ZIKA |
| 25 | 200540286 | SERUM | NYSDOH | NYS-approved LDT (Lanciotti et al) | 29.64 | 20.48 | ZIKA |
| 26 | 200541176 | SERUM | NYSDOH | NYS-approved LDT (Lanciotti et al) | 33.52 | 27.48 | ZIKA |
| 27 | 200549845 | SERUM | NYSDOH | NYS-approved LDT (Lanciotti et al) | 36.56 | 33.98 | ZIKA |
| 28 | 200551095 | SERUM | NYSDOH | NYS-approved LDT (Lanciotti et al) | 31.35 | 27.88 | ZIKA |
| 39 | 200556058 | SERUM | NYSDOH | NYS-approved LDT (Lanciotti et al) | 30.42 | 31.43 | ZIKA |
| 30 | 200563726 | SERUM | NYSDOH | NYS-approved LDT (Lanciotti et al) | 33.17 | 33.55 | ZIKA |
| 31 | 200541052 | SERUM | NYSDOH | NYS-approved LDT (Lanciotti et al) | 33.18 | 31.79 | ZIKA |
| 32 | 200541933 | SERUM | NYSDOH | NYS-approved LDT (Lanciotti et al) | 32.82 | 27.89 | ZIKA |

TABLE 15

Results of Performance of Assay for ZIKV in Unpaired Urine Samples

|   | Sample ID | Sample Type | Tests performed at | Reference Assay used | Reference Assay (Ct for LightMix or S/CO for Aptima) | CII ArboViroPlex rRT PCR Assay (Ct) | Known or Potential Positive Agent |
|---|-----------|-------------|--------------------|----------------------|------------------------------------------------------|-------------------------------------|-----------------------------------|
| 1 | 1043-TDS-0127 | URINE | Boca Biolistics | Aptima Zika Virus Assay | 31.92 | 34.02 | ZIKA |
| 2 | 1043-TDS-0216 | URINE | Boca Biolistics | Aptima Zika Virus Assay | 30.37 | 29.43 | ZIKA |
| 3 | 1043-TDS-0085 | URINE | Boca Biolistics | Aptima Zika Virus Assay | 15.93 | 37.44 | ZIKA |
| 4 | 1043-TDS-0269 | URINE | Boca Biolistics | Aptima Zika Virus Assay | 18.79 | 30.72 | ZIKA |
| 5 | 1043-TDS-0230 | URINE | Boca Biolistics | Aptima Zika Virus Assay | 33.14 | 29.4 | ZIKA |
| 6 | 1043-TDS-0223 | URINE | Boca Biolistics | Aptima Zika Virus Assay | 33.16 | 27.8 | ZIKA |

TABLE 15-continued

Results of Performance of Assay for ZIKV in Unpaired Urine Samples

| Sample ID | Sample Type | Tests performed at | Reference Assay used | Reference Assay (Ct for LightMix or S/CO for Aptima) | CII ArboViroPlex rRT PCR Assay (Ct) | Known or Potential Positive Agent |
|---|---|---|---|---|---|---|
| 7 1043-TDS-0195 | URINE | Boca Biolistics | Aptima Zika Virus Assay | 25.65 | 29.28 | ZIKA |
| 8 1043-TDS-0340 | URINE | Boca Biolistics | Aptima Zika Virus Assay | 35.58 | 25.78 | ZIKA |
| 9 200508712 | URINE | NYSDOH | NYS-approved LDT (Lanciotti et al) | 37.23 | 28.2 | Zika |
| 10 IDR1600009319 | URINE | NYCDOHMH | NYS-approved LDT (Lanciotti et al) | 27.4 | 27.86 | Zika |
| 11 IDR1600009533 | URINE | NYCDOHMH | NYS-approved LDT (Lanciotti et al) | 31.4 | 30.91 | Zika |
| 12 IDR1600010299 | URINE | NYCDOHMH | NYS-approved LDT (Lanciotti et al) | 28.5 | 29.11 | Zika |
| 13 IDR1600010617 | URINE | NYCDOHMH | NYS-approved LDT (Lanciotti et al) | 30.5 | 32.09 | Zika |
| 14 IDR1600010629 | URINE | NYCDOHMH | NYS-approved LDT (Lanciotti et al) | 31.4 | 33.15 | Zika |
| 15 IDR1600033142-02 | URINE | NYSDOH | NYS-approved LDT (Lanciotti et al) | 37.03 | 30.19 | ZIKA |
| 16 IDR1600032961-02 | URINE | NYSDOH | NYS-approved LDT (Lanciotti et al) | 32.81 | 35.58 | ZIKA |
| 17 IDR1600035343-02 | URINE | NYSDOH | NYS-approved LDT (Lanciotti et al) | 36.81 | 32.95 | ZIKA |

TABLE 16

Results of Performance of Assay for ZIKV in Contrived Urine and Serum Samples

| | Ct measured in contrived ZIKV samples in urine | | Ct measured in contrived ZIKV samples in serum | |
|---|---|---|---|---|
| | 1X LoD | 3X LoD | 1X LoD | 3X LoD |
| 1 | 31.04 | 28.76 | 30.56 | 29.71 |
| 2 | 32.19 | 29.11 | 31.25 | 29.69 |
| 3 | 29.71 | 29.17 | 30.25 | 28.51 |
| 4 | 31.23 | 29.06 | 30.53 | 30.71 |
| 5 | 31.14 | 29.30 | 32.10 | 32.60 |
| 6 | 31.44 | 29.24 | 33.16 | 30.52 |
| 7 | 31.29 | 28.42 | 31.24 | 29.01 |
| 8 | 30.76 | 28.82 | 33.21 | 32.27 |
| 9 | 30.29 | 28.58 | 30.97 | 28.68 |
| 10 | 31.15 | 29.44 | 33.70 | 30.55 |
| 11 | 31.37 | 28.67 | 31.01 | 27.47 |
| 12 | 32.33 | 29.07 | 33.50 | 36.66 |
| 13 | 30.99 | 31.54 | 32.61 | 28.57 |
| Average Ct | 31.15 | 29.17 | 31.84 | 30.38 |
| Call rate | 13/13 | 13/13 | 13/13 | 13/13 |
| Call % | 100% | 100% | 100% | 100% |

Example 11—Clinical Evaluation of Dengue Virus

The performance characteristics of CII-ArboPlex rRT-PCR assay for detection of DENV in clinical serum samples were established using the materials and methods set forth in Example 1-5 and in particular primers SEQ ID NOs: 7-9 and probe SEQ ID NO: 10, and 29 DENV positive clinical human serum samples (4 DENV-1, 4 DENV-2, 6 DENV-3, 3 DENV-4 and 12 DENV positives for which serotype data was not available) (Table 17). In addition to clinical samples, 26 contrived serum samples were also used for validation (FIG. 2). For preparing contrived samples 13 negative control serum samples collected from individual patients with febrile illness but no indication of viral infection were spiked with DENV3 at 1× LoD and 3× LoD). Positive DENV clinical serum specimens were collected at NYC-DOHMH, NYSDOH, Fundacao Oswaldo Cruz (FIOCRUZ, Brazil) and The Center for infection and Immunity (Columbia University). The comparator assays used to identify DENV positive samples were the CDC Trioplex Real-time RT-PCR Assay (CII and FIOCRUZ) and Dengue virus real-time RT-PCR assay (FDA-approved CDC assay-KK0128) at NYCDOHMH and NYSDOH. Results for clinical sample evaluation for DENV1-4 with CII-ArboViroPlex rRT-PCR assay are described in Table 17. In all cases the CII-ArboPlex rRT-PCR assay using Primers SEQ ID NOs: 7, 8 and 9 and Probe SEQ ID NO: 10 was positive for the DENV positive samples.

Summary of Clinical samples evaluation for Dengue Virus with CII-ArboPlex rRT-PCR assay using Primers SEQ ID NOs: 7-9 and Probe SEQ ID NO: 10.

Total Serum Samples n=56 positive serum samples
Clinical n=29
Contrived n=26 (n=13 at 1× LoD, this being 4.63 E+03 GEQ/ml and n=13 at 3× LoD, this being 1.39 E+04 GEQ/ml)

TABLE 17

Validation of CII-ArboPlex rRT-PCR assay with Dengue Positive Clinical Samples

| | Sample ID | Sample Type | Tests performed at | Reference Assay used | Reference Assay (Ct for LightMix or S/CO for Aptima) | CII ArboViroPlex rRT PCR Assay (Ct) | Known or Potential Positive Agent |
|---|---|---|---|---|---|---|---|
| 1 | SND-01 | SERUM | Columbia University | Trioplex Real-time RT-PCR Assay | 37.89 | 34.2 | Dengue |
| 2 | SND-16 | SERUM | Columbia University | Trioplex Real-time RT-PCR Assay | 33.43 | 32.26 | Dengue |
| 3 | SND-28 | SERUM | Columbia University | Trioplex Real-time RT-PCR Assay | 39.09 | 36.63 | Dengue |
| 4 | SND-29 | SERUM | Columbia University | Trioplex Real-time RT-PCR Assay | 33.84 | 27.1 | Dengue |
| 5 | SND-168 | SERUM | Columbia University | Trioplex Real-time RT-PCR Assay | 38.9 | 31.82 | Dengue |
| 6 | SND-07 | SERUM | Columbia University | Trioplex Real-time RT-PCR Assay | 36.21 | 29 | Dengue |
| 7 | SND-19 | SERUM | Columbia University | Trioplex Real-time RT-PCR Assay | 32.85 | 23.27 | Dengue |
| 8 | CG48 | SERUM | FIOCRUZ, Brazil | Trioplex Real-time RT-PCR Assay | 30.27 | 34.04 | Dengue |
| 10 | CG8A | SERUM | FIOCRUZ, Brazil | Trioplex Real-time RT-PCR Assay | 34.78 | 35.45 | Dengue |
| 11 | CG96 | SERUM | FIOCRUZ, Brazil | Trioplex Real-time RT-PCR Assay | 37.5 | 36.47 | Dengue |
| 12 | CG83 | SERUM | FIOCRUZ, Brazil | Trioplex Real-time RT-PCR Assay | 33.6 | 26.04 | Dengue |
| 13 | CG100 | SERUM | FIOCRUZ, Brazil | Trioplex Real-time RT-PCR Assay | 29.39 | 21.98 | Dengue |
| 14 | BRA 68 | SERUM | Columbia University | Trioplex Real-time RT-PCR Assay | 21.85 | 20.28 | Dengue 1 |
| 15 | BRA 73 | SERUM | Columbia University | Trioplex Real-time RT-PCR Assay | 25.73 | 25.96 | Dengue 1 |
| 16 | VEL16-16 | SERUM | NYSDOH | FDA-approved CDC assay | 36.94 | 29.65 | Dengue 1 |
| 17 | VEL16-10 | SERUM | NYSDOH | FDA-approved CDC assay | 32.5 | 28.87 | Dengue 1 |
| 18 | BRA 75 | SERUM | Columbia University | Trioplex Real-time RT-PCR Assay | 35.06 | 33.49 | Dengue 2 |
| 19 | BRA 96 | SERUM | Columbia University | Trioplex Real-time RT-PCR Assay | 27.43 | 26.35 | Dengue 2 |
| 20 | VEL16-13 | SERUM | NYSDOH | FDA-approved CDC assay | 33.87 | 30.26 | Dengue 2 |
| 21 | VEL16-15 | SERUM | NYSDOH | FDA-approved CDC assay | 30.24 | 28.32 | Dengue 2 |
| 22 | BRA 121 | SERUM | Columbia University | Trioplex Real-time RT-PCR Assay | 29.35 | 31.98 | Dengue 3 |
| 23 | BRA 122 | SERUM | Columbia University | Trioplex Real-time RT-PCR Assay | 32.64 | 26.08 | Dengue 3 |
| 24 | SND 22 | SERUM | Columbia University | Trioplex Real-time RT-PCR Assay | 32.51 | 27.77 | Dengue 3 |
| 25 | VEL16-14 | SERUM | NYSDOH | FDA-approved CDC assay | 34.57 | 29.2 | Dengue 3 |
| 26 | VEL16-08 | SERUM | NYSDOH | FDA-approved CDC assay | 30.99 | 23.92 | Dengue 3 |
| 27 | VEL16-11 | SERUM | NYSDOH | FDA-approved CDC assay | 37.25 | 28.62 | Dengue 3 |
| 28 | DENV 4266 | SERUM | Columbia University | Trioplex Real-time RT-PCR Assay | 33.64 | 26.19 | Dengue 4 |
| 29 | VEL16-12 | SERUM | NYSDOH | FDA-approved CDC assay | 31.01 | 26.85 | Dengue 4 |
| 30 | VEL16-09 | SERUM | NYSDOH | FDA-approved CDC assay | 35.96 | 26.64 | Dengue 4 |

Example 12—Chikungunya Virus Clinical Evaluation

The performance characteristics of CII-ArboPlex rRT-PCR assay for detection of CHIKV were established using the materials and methods set forth in Example 1-5 and in particular primers SEQ ID NOs: 11 and 12, and probe SEQ ID NO: 13, and 20 CHIKV positive samples (Table 18). Positive CHIKV specimens were collected at University of the West Indies, Trinidad. The CDC Trioplex Real-time RT-PCR Assay was used as the comparator assay to generate CHIKV positive data at Columbia University. In addition to clinical samples, 26 contrived serum samples (13 serum samples were spiked with CHIKV at 1× LoD and 3× LoD) were also used for validation (FIG. 2). In all cases the CII-ArboPlex rRT-PCR assay using Primers SEQ ID NOs: 11 and 12 and Probe SEQ ID NO: 13 was positive for the CHIKV positive samples.

Summary of Clinical samples evaluation for chikungunya virus with CII-ArboPlex rRT-PCR assay using Primers SEQ ID NOs: 11 and 12 and Probe SEQ ID NO: 13.

Total Samples n=46 positive serum samples
Clinical n=20
Contrived n=26 (n=13 at 1× LoD, this being 3.65 E+02 GEQ/ml and n=13 at 3× LoD, this being 1.09 E+04 GEQ/ml)

Example 13—West Nile Virus Clinical Evaluation

The performance characteristics of CII-ArboPlex rRT-PCR assay for detection of CHIKV were established using the materials and methods set forth in Example 1-5 and in particular primers SEQ ID NOs: 4 and 5, and probe SEQ ID NO: 6, and 19 WNV positive serum samples (Table 19). Positive WNV specimens were collected by the Blood

TABLE 18

Validation of CII-ArboPlex rRT-PCR assay with Chikungunya positive clinical samples

| S. No. | Sample ID | Sample Type | Reference tests performed at | Reference Assay used | Reference Assay (Ct) | CII ArboViroPlex rRT PCR Assay (Ct) | Known or Potential Positive Agent |
|---|---|---|---|---|---|---|---|
| 1 | 090914-010 | Serum | Columbia University | Trioplex Real-time RT-PCR Assay | 29.793 | 31.16 | Chikungunya Virus |
| 2 | 040914-020 | Serum | Columbia University | Trioplex Real-time RT-PCR Assay | 28.761 | 30.51 | Chikungunya Virus |
| 3 | 230914-020 | Serum | Columbia University | Trioplex Real-time RT-PCR Assay | 22.15 | 22.21 | Chikungunya Virus |
| 4 | 250914-030 | Serum | Columbia University | Trioplex Real-time RT-PCR Assay | 25.056 | 25.7 | Chikungunya Virus |
| 5 | 300814-020 | Serum | Columbia University | Trioplex Real-time RT-PCR Assay | 21.33 | 21.51 | Chikungunya Virus |
| 6 | 190914-020 | Serum | Columbia University | Trioplex Real-time RT-PCR Assay | 27.684 | 28.06 | Chikungunya Virus |
| 7 | 031114-030 | Serum | Columbia University | Trioplex Real-time RT-PCR Assay | 27.205 | 27.4 | Chikungunya Virus |
| 8 | 170914-DM | Serum | Columbia University | Trioplex Real-time RT-PCR Assay | 23.946 | 23.17 | Chikungunya Virus |
| 9 | 200914-030 | Serum | Columbia University | Trioplex Real-time RT-PCR Assay | 20.166 | 18.97 | Chikungunya Virus |
| 10 | 110914-020 | Serum | Columbia University | Trioplex Real-time RT-PCR Assay | 20.343 | 19.71 | Chikungunya Virus |
| 11 | 031114-010 | Serum | Columbia University | Trioplex Real-time RT-PCR Assay | 22.965 | 22.28 | Chikungunya Virus |
| 12 | 180914-050 | Serum | Columbia University | Trioplex Real-time RT-PCR Assay | 20.556 | 20.03 | Chikungunya Virus |
| 13 | 041114-030 | Serum | Columbia University | Trioplex Real-time RT-PCR Assay | 15.902 | 13.79 | Chikungunya Virus |
| 14 | 250814-020 | Serum | Columbia University | Trioplex Real-time RT-PCR Assay | 27.094 | 29.4 | Chikungunya Virus |
| 15 | 160914-060 | Serum | Columbia University | Trioplex Real-time RT-PCR Assay | 20.413 | 19.9 | Chikungunya Virus |
| 16 | 150914-020 | Serum | Columbia University | Trioplex Real-time RT-PCR Assay | 20.123 | 19.84 | Chikungunya Virus |
| 17 | 110914-030 | Serum | Columbia University | Trioplex Real-time RT-PCR Assay | 23.612 | 22.54 | Chikungunya Virus |
| 18 | 031114-031 | Serum | Columbia University | Trioplex Real-time RT-PCR Assay | 27.633 | 26.2 | Chikungunya Virus |
| 19 | 041114-031 | Serum | Columbia University | Trioplex Real-time RT-PCR Assay | 15.655 | 13.26 | Chikungunya Virus |
| 20 | 150914-021 | Serum | Columbia University | Trioplex Real-time RT-PCR Assay | 20.714 | 19.66 | Chikungunya Virus |

System Research Institute and sample were tested positive for WNV by Creative Testing Solutions, Phoenix, Ariz. using the FDA-approved Procleix® WNV TMA Assay. The WNV-NS3 RT-PCR Assay (PMID: 10821368) was used with slight modification as the comparator assay to generate WNV real-time data at Columbia University. In addition to clinical samples, 26 contrived serum samples (13 serum samples were spiked with WNV at 1× LoD and 3× LoD) were also used for validation (FIG. 2). In all cases the CII-ArboPlex rRT-PCR assay using Primers SEQ ID NOs: 4 and 5 and Probe SEQ ID NO: 6 was positive for the WNV positive samples.

Summary of Clinical samples evaluation for West Nile virus with CII-ArboPlex rRT-PCR assay using Primers SEQ ID NOs: 4 and 5 and Probe SEQ ID NO: 6.

Total Samples n=45 positive serum samples
Clinical n=19
Contrived n=26 (n=13 at 1× LoD, this being 2.12 E+02 GEQ/ml and n=13 at 3× LoD, this being 6.36 E+02 GEQ/ml)

Example 14—Validation of CII-ArboPlex rRT-PCR Assay with Contrived Serum and Urine Samples Spiked with Dengue, Chikungunya and West Nile Viruses Thirteen serum and urine samples were each spiked with DENV (serotype 3), CHIKV or WNV at 1× LoD and 2× LoD (26 DENV serum samples, 26 DENV urine samples, 26 CHIKV serum samples, 26 CHIKV urine samples, 26 WNV serum samples, 26 WNV urine samples) were tested using the materials and methods set forth in Examples 1-5 and 11-13 and the primers and probe set forth in Table 2 specific for DENV, CHIKV, and WNV. As assay specificity controls a panel of serum samples from febrile Lyme disease patients (26) and urine samples (26) collected at NYSDOH from subjects with suspicion of ZIKV infection but negative by PCR for all arboviruses was used. In all cases 100% of the viruses were detected. Data for samples is shown in FIG. 2.

TABLE 19

Validation of CII-ArboPlex rRT-PCR Assay with West Nile Virus Positive Clinical Samples

| S. No. | Sample ID | Sample Type | Reference tests performed at | Reference Assay used | Procleix S/CO Ratio (1:8 dilution0 | CII WNV-NS3 RT-PCR Assay (Ct) | CII ArboViroPlex rRT PCR Assay (Ct) | Known or Potential Positive Agent |
|---|---|---|---|---|---|---|---|---|
| 1 | IL17-001 | Serum | BSRI/CTS | Procleix ® WNV Assay | 35.52 | 27.28 | 27.13 | West Nile Virus |
| 2 | IL17-002 | Serum | BSRI/CTS | Procleix ® WNV Assay | 30.67 | 35.48 | 36.80 | West Nile Virus |
| 3 | IL17-003 | Serum | BSRI/CTS | Procleix ® WNV Assay | 33.77 | 30.13 | 30.61 | West Nile Virus |
| 4 | IL17-004 | Serum | BSRI/CTS | Procleix ® WNV Assay | 32.76 | 28.65 | 28.40 | West Nile Virus |
| 5 | IL17-005 | Serum | BSRI/CTS | Procleix ® WNV Assay | 31.36 | 33.91 | 34.85 | West Nile Virus |
| 6 | IL17-006 | Serum | BSRI/CTS | Procleix ® WNV Assay | 29.60 | 33.47 | 37.02 | West Nile Virus |
| 7 | IL17-007 | Serum | BSRI/CTS | Procleix ® WNV Assay | 30.99 | 30.64 | 31.13 | West Nile Virus |
| 8 | IL17-008 | Serum | BSRI/CTS | Procleix ® WNV Assay | 33.84 | 31.64 | 32.04 | West Nile Virus |
| 9 | IL17-009 | Serum | BSRI/CTS | Procleix ® WNV Assay | 26.20 | 29.03 | 29.09 | West Nile Virus |
| 10 | IL17-010 | Serum | BSRI/CTS | Procleix ® WNV Assay | 27.82 | 29.26 | 29.97 | West Nile Virus |
| 11 | IL17-011 | Serum | BSRI/CTS | Procleix ® WNV Assay | 27.40 | 26.59 | 26.25 | West Nile Virus |
| 12 | IL17-012 | Serum | BSRI/CTS | Procleix ® WNV Assay | 27.34 | 33.08 | 32.99 | West Nile Virus |
| 13 | IL17-013 | Serum | BSRI/CTS | Procleix ® WNV Assay | 31.33 | 26.21 | 26.61 | West Nile Virus |
| 14 | IL17-014 | Serum | BSRI/CTS | Procleix ® WNV Assay | 30.39 | 32.40 | 33.31 | West Nile Virus |
| 15 | IL17-015 | Serum | BSRI/CTS | Procleix ® WNV Assay | 29.96 | 28.50 | 28.99 | West Nile Virus |
| 16 | IL17-016 | Serum | BSRI/CTS | Procleix ® WNV Assay | 32.09 | 33.73 | 32.50 | West Nile Virus |
| 17 | IL17-017 | Serum | BSRI/CTS | Procleix ® WNV Assay | 31.93 | 31.20 | 32.44 | West Nile Virus |
| 18 | IL17-018 | Serum | BSRI/CTS | Procleix ® WNV Assay | 32.58 | 26.65 | 26.61 | West Nile Virus |
| 19 | IL17-019 | Serum | BSRI/CTS | Procleix ® WNV Assay | 34.87 | 28.15 | 28.25 | West Nile Virus |

REFERENCES

Broutet et al. *N. Engl. J. Med.* 2016 Apr. 21; 374(16):1506-9.

Rasmussen et al. *N. Engl. J. Med.* 2016 May 19; 374(20): 1981-7.

CDC Website

Driggers et al. *New England Journal of Medicine* Zika virus Infection with Prolonged Maternal Viremia and Fetal Brian Abnormalities, Jun. 2, 2016; 374:2142-2151.

Meaney-Delman et al. *Obstetrics and Gynecology* Prolonged Detection of Zika Virus RNA in Pregnant Women, 2016 October; 128(4) 724-730.

Lanciotti et al. *Emerg Infect Dis* Genetic and serologic properties of Zika virus associated with an epidemic, Yap State, Micronesia, 2007. 2008; 14:1232-9.

Briese et al. *Lancet* Detection of West Nile virus sequences in cerebrospinal fluid. 2000 May 6; 355(9215):1614-5.

What is claimed is:

1. A method of differentially detecting the presence of the Zika virus, dengue virus (genotype 1-4), chikungunya virus, and West Nile virus, in a sample comprising:
    contacting the sample with at least one primer specific the Zika virus and at least one primer specific for each of dengue virus (genotype 1-4), chikungunya virus, and West Nile virus, wherein the primers allow the differential detection of Zika virus from dengue virus (genotype 1-4), chikungunya virus, and West Nile virus;
    subjecting the sample and the primers to amplification conditions;
    detecting the presence of amplification product, wherein the presence of amplification product from the primer specific to Zika virus indicates the presence of nucleic acid from Zika virus in the sample, and the presence of amplification product from the primer specific for dengue virus (genotype 1-4), Chikungunya virus, and West Nile virus indicates the presence of nucleic acid from that virus in the sample.

2. The method of claim 1, further comprising contacting the sample with a probe specific for Zika virus, dengue virus (genotype 1-4), chikungunya virus, and West Nile virus.

3. The method of claim 1, wherein the sample is of natural origin and is chosen from the group consisting of plasma, serum, whole blood, spinal fluid, semen, amniotic fluid, lymph fluid, synovial fluid, urine, tears, blood cells, organs, and tissue.

4. The method of claim 1, wherein the sample is urine or serum.

5. The method of claim 1, wherein the sample is from a human subject.

6. The method of claim 1, wherein the nucleic acid is RNA.

7. The method of claim 2, wherein the primers and probe specific for Zika virus are from the 3'UTR of the viral genome.

8. The method of claim 7, wherein the primers comprise SEQ ID NOs: 1 and 2, and the probe comprises SEQ ID NO: 3.

9. A method of detecting the presence of the Zika virus and at least one other virus chosen from the group consisting of dengue virus (genotype 1-4), chikungunya virus, and West Nile virus, in a sample comprising:
    contacting the sample with primers specific the Zika virus comprising SEQ ID NOs: 1 and 2, and at least one primer specific from another virus chosen from the group consisting of dengue virus (genotype 1-4), chikungunya virus, and West Nile virus;

subjecting the sample and the primers to amplification conditions;

further contacting the sample with a probe comprising SEQ ID NO: 3 and wherein the probe comprises a 5' modification of CAL Fluor Red 610 and a 3' modification of BHQ-2; and detecting the presence of amplification product, wherein the presence of amplification product from the primer specific to Zika virus indicates the presence of nucleic acid from Zika virus in the sample, and the presence of amplification product from the primer specific for the at least one virus chosen from the group consisting of dengue virus (genotype 1-4), Chikungunya virus, and West Nile virus indicates the presence of nucleic acid from that virus in the sample.

10. The method of claim 2, wherein the primers and probe specific for dengue virus (genotype 1-4) are from the 3'UTR of the viral genome.

11. The method of claim 6, wherein the primers comprise SEQ ID NOs: 7, 8, and 9, and the probe comprises SEQ ID NO: 10.

12. The method of claim 7, wherein the probe comprises a 5' modification of CAL Fluor Orange 560 and a 3' modification of BHQ-1Plus.

13. The method of claim 2, wherein the primers and probe specific for Chikungunya virus are from the NSP2 portion of the viral genome.

14. The method of claim 9, wherein the primers comprise SEQ ID NOs: 11 and 12, and the probe comprises SEQ ID NO: 13.

15. The method of claim 10, wherein the probe comprises a 5' modification of FAM and a 3' modification of BHQ-1Plus.

16. The method of claim 2, wherein the primers and probe specific for West Nile virus are from the NS5 portion of the viral genome.

17. The method of claim 16, wherein the primers comprise SEQ ID NOs: 4 and 5, and the probe comprise SEQ ID NO: 6.

18. The method of claim 17, wherein the probe comprises a 5' modification of Quasar 670 and a 3' modification of BHQ-2.

19. A kit for the simultaneous detection and differentiation of Zika virus and at least one other virus chosen from the group consisting of dengue virus (genotype 1-4), chikungunya virus, and West Nile virus, comprising: primers comprising SEQ ID NOs: 1, 2, 4, 5, 7, 8, 9, 11, and 12; and probes comprising SEQ ID NOs: 3, 6, 10, and 13.

20. The kit of claim 19, further comprising reagents for performing the differential detection comprising control sequences, nucleic acid polymerase and nucleic acid extraction reagents; and instructions for use.

21. The kit of claim 19, wherein the primers and probes for the detection of each virus are in a single reaction mixture.

22. The kit of claim 19, wherein the probes further comprise a detectable label.

23. A synthetic nucleic acid with a nucleic acid sequence selected from any of one of SEQ ID NOs: 1-13.

24. The method of claim 7, wherein the primers consist of SEQ ID NOs: 1 and 2, and the probe consists of SEQ ID NO: 3.

* * * * *